United States Patent [19]

Bally et al.

[11] Patent Number: 5,077,056
[45] Date of Patent: Dec. 31, 1991

[54] ENCAPSULATION OF ANTINEOPLASTIC AGENTS IN LIPOSOMES

[75] Inventors: Marcel B. Bally; Pieter R. Cullis; Michael J. Hope; Thomas D. Madden; Lawrence D. Mayer, all of Vancouver, Canada

[73] Assignee: The Liposome Company, Inc., Princeton, N.J.

[21] Appl. No.: 284,751

[22] Filed: Dec. 12, 1988

Related U.S. Application Data

[63] Continuation of Ser. No. 749,161, Jun. 26, 1985, abandoned, which is a continuation-in-part of Ser. No. 638,809, Aug. 8, 1984, abandoned.

[51] Int. Cl.$^5$ .......................... B01J 13/02; A61K 9/52
[52] U.S. Cl. .................................... 424/450; 436/829
[58] Field of Search ............... 424/450, 417; 514/183, 514/459, 33, 34, 283; 428/402; 436/829

[56] References Cited

U.S. PATENT DOCUMENTS

| | | | |
|---|---|---|---|
| 3,962,429 | 6/1976 | Furuno et al. | 424/181 |
| 3,993,754 | 11/1976 | Rahman et al. | 424/177 |
| 4,016,100 | 4/1977 | Suzuki et al. | 252/316 |
| 4,193,983 | 3/1980 | Ullman et al. | 424/12 |
| 4,217,344 | 8/1980 | Vanlerberghe et al. | 252/316 |
| 4,235,871 | 11/1980 | Papahadjopoulos et al. | 252/316 |
| 4,241,046 | 12/1980 | Papahadjopoulos et al. | 424/19 |
| 4,370,349 | 1/1983 | Evans et al. | 514/785 |
| 4,372,949 | 2/1983 | Kodama et al. | 424/38 |
| 4,389,330 | 6/1983 | Tice et al. | 264/4.1 |
| 4,397,846 | 8/1983 | Weiner et al. | 424/199 |
| 4,411,894 | 10/1983 | Schrank et al. | 424/199 |
| 4,419,348 | 12/1983 | Rahman et al. | 514/34 |
| 4,460,577 | 7/1984 | Moro et al. | 424/180 |
| 4,485,045 | 11/1984 | Regen | 264/4.3 |
| 4,515,736 | 5/1985 | Deamer | 264/4.3 |
| 4,529,561 | 7/1985 | Hunt et al. | 424/450 |
| 4,532,089 | 7/1985 | MacDonald et al. | 264/4.3 |
| 4,769,250 | 9/1988 | Forssen | 424/450 |
| 4,946,683 | 8/1990 | Forrsen | 429/450 |

FOREIGN PATENT DOCUMENTS

| | | | |
|---|---|---|---|
| WO86/00238 | 1/1986 | PCT Int'l Appl. | |
| 2022319B | 2/1982 | United Kingdom | 424/450 |
| 2134869 | 8/1984 | United Kingdom | |
| 88/09168 | 1/1988 | World Int. Prop. O. | 424/450 |

OTHER PUBLICATIONS

McLaughlin et al., J. Gen. Physiol., 1981, 77(4) 445-73, Chemical Abs., vol. 94, 1981, Abstract 169846g.
Corda, et al., J. Membr. Biol., 1982, 65(3) 235-42, Chem. Abs., vol. 96, 1982, Abs. 176569p.
Cafiso, et al., Biophys. J., 1983, 44(1) 49-57, Chem. Abs., vol. 99, 1983, Abs. 171669y.
Mayhew et al., Biol. Cell (1981) 1983 47(1) 81-5, Chem. Abs., vol. 98, 1983, Abs. 221734t.
Chemical Abstracts 103:76141n, Mayer et al.
Chemical Abstracts 103:174355e.
Chemical Abstracts 99:49240m.
Deamer, et al., "The Response of Fluorescent Amines to pH Gradients Across Liposome Membranes", 1972, Biochim. Biophys. Acta, 274, pp. 323-335.
Kornberg, et al., "Measurement of Transmembrane Potentials in Phospholipid Vesicles", 1972, Proc. Nat. Aca. Sci USA 69(6), pp. 1508-1513.

(List continued on next page.)

Primary Examiner—Mukund J. Shah
Assistant Examiner—E. C. Ward
Attorney, Agent, or Firm—Allen Bloom; Catherine L. Kurtz

[57] ABSTRACT

Methods for encapsulating ionizable antineoplastic agents in liposomes using transmembrane potentials are provided. Trapping efficiencies approaching 100% and rapid loading are readily achieved. Dehydration protocols which allow liposomes to be conveniently used in the administration of antineoplastic agents in a clinical setting are also provided. In accordance with other aspects of the invention, transmembrane potentials are used to reduce the rate of release of ionizable drugs from liposomes.

20 Claims, 13 Drawing Sheets

OTHER PUBLICATIONS

Nichols and Deamer, "Catecholamine Uptake and Concentration by Liposomes Maintaining pH Gradients", 1976, Biochim. Biophys. Acta 455, pp. 269–271.

Casey et al., "Active Proton Uptake by Chromaffin Granules: Observation by Amine Distribution and Phosphorus-31 Nuclear Magnetic Resonance Techniques", 1977, Biochemistry 16(5) pp. 972–976.

Cramer and Prestegard, "NMR Studies of pH-Induced Transport of Carboxylic Acids Across Phospholipid Vesicle Membranes", Biochem. Biophys. Res. Commun., 1977, 75(2) pp. 295–301.

Kano and Fendler, "Pyranine as a Sensitive pH Probe for Liposome Interiors and Surfaces", Biochim. Biophys. Acta, 1978, 509, pp. 289–299.

Kirby and Gregoriadis, "The Effect of Lipid Composition of Small Unilamellar Liposomes Containing Melphalan and Vincristine on Drug Clearance After Injection into Mice", Abstract of Biochem. Pharmacol., 1983, 32(4) pp. 609–615.

Burke et al., Chem. Abstracts, vol. 102, No. 3, Jan. 21, 1985.

Crommelin, et al., "Stability of Liposomes on Storage: Freeze Dried, Frozen or as an Aqueous Dispersion", Phar. Res. (1984) pp. 159–163.

Herbette, et al., Chem. Abstracts, vol. 99, No. 23, Dec. 5, 1983.

Bottcher, et al., 1961, Anal. Chim. Acta., 24:203–204, "A Rapid and Sensitive Sub-Micro Phosphorus Determination".

Jonah, et al., 1975, Biochim. et Biophys. Acta, 401:336–348, "Tissue Distribution of EDTA Encapsulated Within Liposomes of Varying Surface Properties".

Chen, et al., 1956, Analytical Chem., 11:1756–1758, "Microdetermination of Phosphorus".

Singleton, et al., 1965, J. Am. Oil Chem. Soc., 42:53–56, "Chromatographically Homogeneous Lecithin from Egg Phospholipids".

Pick, 1981, Arch. Biochem. Biophys., 212(1), 186–194, "Liposomes with a Large Trapping Capacity Prepared by Freezing and Thawing of Sonicated Phosphilopid Mixtures".

Morii, et al., 1983, Int. J. Pharm., 17(2–3) 215–224, "Size and Permeability of Liposomes Extruded Through Polycarbonate Membranes".

Kirby, et al., 1984, in *Liposome Technology*, vol. 1, Preparation of Liposomes, G. Gregoriadis, et., pp. 19–27, "A Simple Procedure for Preparing Liposomes Capable of High Encapsulation Efficiency Under Mild Conditions".

Forssen, et al., 1983, Cancer Res., 43:546, "Improved Therapeutic Benefits of Doxorubicin by Entrapment in Anionic Liposomes".

Gabizon, et al., 1982, Cancer Res., 42–4734, "Liposomes as in Vivo Carriers of Adriamycin: Reduced Cardiac Uptake and Preserved Antitumor Activity in Mice".

Olson, Eur. J. Cancer Clin. Oncol., 18:167, "Characterization, Toxicity and Therapeutic Efficacy of Adriamycin Encapsulated in Liposomes".

Abra, et al., 1983, Cancer Chemother. Pharmacol., 11:98, "Delivery of Therapeutic Doses of Doxorubicin in the Mouse Lung Using Lung-Accumulating Liposomes Proves Unsuccessful".

Rahman, et al., 1982, Cancer Res., 42:1817, "Doxorubicin-Induced Chronic Cardiotoxicity and Its Protection by Liposomal Administration".

Rosa, et al., 1982, in: Transport in Biomembranes, 1982, R. Antolini et al., (eds.), Raven Press, New York, "Liposomes Containing Doxorubicin: An Example of Drug Targeting".

Rosa, et al., 1983, Pharmacol., 26:221, "Absorption and Tissue Distribution of Doxorubicin Entrapped in Liposomes Following Intravenous or Intraperitoneal Administration".

Deamer, 1983, in: Liposomes, 1983, M. Ostro (ed.), Marcel Dekker, New York.

Hope, et al., 19875, Biochim. Biophys. Acta., 812:55, "Production of Large Unilamellar Vesicles by a Rapid Extrusion Procedure. Characterization of Size Distribution, Trapped Volume and Ability to Maintain a Membrane Potential".

Bally, et al., 1985, Biochim. Biophys. Acta., 812:66, "Uptake of Safranine and Other Lipophilic Cations into Model Membrane System in Response to a Membrane Potential".

Papahadjopoulos, et al., 1980, in Liposomes and Immunology, 1980, Tom and Six, eds., Elsevier, New York, "Optimization of Liposomes as a Carrier System for the Intracellular Delivery of Drugs and Macromolecules".

Mauk, et al., 1979, PNAS, USA, 76:765, "Preparation of Lipid Vesicles Containing High Levels of Entrapped (List continued on next page.)

OTHER PUBLICATIONS
Radioactive Cations".

Garcia, et al., 1983, Biochemistry, 22(10):2524, "Mechanism of Lactose Translocation in Proteoliposomes Reconstituted with lac Carrier Protein Purified from *Escherichia coli.* 1. Effect of pH and Imposed Membrane Potential on Efflux, Exchange, and Counterflow".

Shakhov, et al., 1984, Biokhimika, 48(8):1347, "Reconstitution of Highly Purified Proton-Translocating Pyrothosphatase".

Kirby, et al., 1984, Bio/Technology, 2(11):979, "Dehydration-Rehydration Vesicles: A Simple Method for High Yield Drug Entrapment in Liposomes".

Crommelin, et al., 1983, Int. J. Pharm., 16(1):79, "Preparation and Characterization of Doxorubicin-Containing Liposomes: I. Influence of Liposome Charge and pH of Hydration Medium on Loading Capacity and Particle Size".

Kano, et al., 1977, Life Sciences, 20:1729, "Enhanced Uptake of Drugs in Liposomes: Use of Labile Vitamin $B_{12}$ Complexes of 6-Mercaptopurine and 8-Azaguanine".

Nichols, et al., 1976, Biochim. Biophys. Acta., 455:269, "Catecholamine Uptake and Concentration by Liposomes Maintaining pH Gradients".

Akerman, et al., 129767, Biochim. Biophys. Acta., 426:624, "Stacking of Safranine in Liposomes During Valinomycin Induced Efflux of Potassium Ions".

van Hoesel, et al., 1984, Cancer Res., 44:3698, "Reduced Cardiotoxicity and Nephrotoxicity with Preservation of Antitumor Activity of Doxorubicin Entrapped in Stable Liposomes in the LOU/M Wsi Rat".

ENCAPSULATION OF ANTINEOPLASTIC AGENTS IN LIPOSOMES

CROSS REFERENCE TO RELATED APPLICATION

This is a continuation of Ser. No. 749,161 filed June 26, 1985, now abandoned, which is a continuation-in-part of application Ser. No. 638,809, filed Aug. 8, 1984, now abandoned.

BACKGROUND OF THE INVENTION

1. Field of the Invention

This invention relates to antineoplastic agents and in particular to the encapsulation of such agents in liposomes.

2. Description of the Prior Art

As has been established by various investigators, cancer therapy employing antineoplastic agents can in many cases be significantly improved by encapsulating the antineoplastic agent in liposomes, rather than administrating the agent directly into the body. See, for example, Forssen, et. al., (1983), *Cancer Res.*, 43:546; Gabizon, et. al., (1982), *Cancer Res.*, 42:4734; and Olson, et. al., (1982), *Eur. J. Cancer Clin. Oncol.*, 18:167; but see Abra, et. al., (1983), *Cancer Chemother. Pharmacol.*, 11:98. Incorporation of such agents in liposomes changes their antitumor activities, clearance rates, tissue distributions, and toxicities compared to direct administration. See, for example, Rahman, et. al., (1982), *Cancer Res.*, 42:1817; Rosa, et. al., (1982) in *Transport in Biomembranes: Model Systems and Reconstitution*, R. Antolini et. al., ed., Raven Press, New York. 243-256; Rosa, et. al., (1983), *Pharmacology*. 26:221; Forssen, et. al., *supra;* Gabizon, et. al., *supra;* and Olson, et. al., *supra*. For example, it is well known that the cardiotoxicity of the anthracycline antibiotics daunorubicin and doxorubicin (adriamycin) and their pharmaceutically acceptable derivatives and salts can be significantly reduced through liposome encapsulation. See, for example, Forssen, et. al., *supra;* Olson, et. al., *supra;* and Rahman, et. al., *supra*. Also, incorporation of highly toxic antineoplastic agents in liposomes can reduce the risk of exposure to such agents by persons involved in their administration.

The use of liposomes to administer antineoplastic agents has raised problems with regard to both drug encapsulation and drug release during therapy. With regard to encapsulation, there has been a continuing need to increase trapping efficiencies so as to minimize the lipid load presented to the patient during therapy. In addition, high trapping efficiencies mean that only a small amount of drug is lost during the encapsulation process, an important advantage when dealing with the expensive drugs currently being used in cancer therapy.

As to drug release, many antineoplastic agents, such as adriamycin, have been found to be rapidly released from liposomes after encapsulation. Such rapid release diminishes the beneficial effects of liposome encapsulation and thus, in general, is undesirable. Accordingly, there have been continuing efforts by workers in the art to find ways to reduce the rate of release of antineoplastic agents and other drugs from liposomes.

In addition to these problems with encapsulation and release, there is the overriding problem of finding a commercially acceptable way of providing liposomes containing antineoplastic agents to the clinician. Although the production and loading of liposomes on an "as needed" basis is an acceptable procedure in an experimental setting, it is, in general, unsatisfactory in a clinical setting. Accordingly, there is a significant and continuing need for methods whereby liposomes, with or without encapsulated drugs, can be shipped, stored and in general moved through conventional commercial distribution channels without substantial damage.

SUMMARY OF THE INVENTION

In view of the above state of the art, it is an object of the present invention to provide improved methods for encapsulating antineoplastic agents in liposomes. It is an additional object of the invention to provide methods for reducing the rate of release of antineoplastic agents and other biologically-active agents from liposomes. It is a further object of the invention to provide methods for dehydrating liposomes, either before or after the loading of antineoplastic agents, so that the liposomes can be stored, shipped, and commercially distributed without substantial damage.

To achieve these and other objects, the invention, in accordance with one of its aspects, provides a method for loading liposomes with ionizable antineoplastic agents wherein a transmembrane potential is created across the walls of the liposomes and the antineoplastic agent is loaded into the liposomes by means of the transmembrane potential.

The method can be used with essentially any antineoplastic agent which can exist in a charged state when dissolved in an aqueous medium (e.g., organic compounds which include an amino group which can be protonated). Preferably, the agent should be relatively lipophilic so that it will partition into the liposome membranes. Multiple antineoplastic agents can be loaded either simultaneously or sequentially into liposomes using the method. Also, the liposomes into which the ionizable antineoplastic agents are loaded can themselves be pre-loaded with other antineoplastic agents or other drugs using conventional encapsulation techniques (e.g., by incorporating the drug in the buffer from which the liposomes are made).

In accordance with other aspects of the invention, a method is provided for reducing the rate of release of an ionizable antineoplastic agent or other ionizable biologically-active agent from liposomes wherein a transmembrane potential, oriented to retain the agent in the liposomes, is generated across the liposome membranes. As described in detail below, it has been surprisingly found that such a transmembrane potential is capable of producing a ten-fold reduction in the rate of release of ionizable drugs, such as adriamycin, from liposomes. The method can be used with essentially any ionizable material which can be encapsulated in a liposome. The transmembrane potential can be generated after encapsulation or can be the same transmembrane potential used to load the liposomes in accordance with the encapsulation technique described above.

In accordance with further of its aspects, the invention provides various dehydration protocols which allow liposomes to be conveniently used in the administration of antineoplastic agents in a clinical setting. In accordance with certain of those protocols, antineoplastic agents are loaded into liposomes and the resulting preparation is dehydrated so that it can be conveniently stored, shipped or otherwise handled without substantial leakage of the antineoplastic agent from the liposomes.

In accordance with certain embodiments of this protocol, the dehydration is done in the presence of one or more protective sugars. Preferably, the one or more sugars are present at both the inside and outside surfaces of the liposome membranes. Further, it is preferred that the sugars be selected from the group consisting of trehalose, maltose, lactose, sucrose, glucose, and dextran, with the most preferred sugars from a performance point of view being trehalose and sucrose. The dehydration is done under vacuum and can take place either with or without prior freezing of the liposome preparation.

In accordance with other embodiments of this protocol, the dehydration is done without the use of a protective sugar. In this case, the dehydration must be done without prior freezing, the liposomes used to encapsulate the antineoplastic agent must be of the type which have -multiple lipid layers, and the liposome preparation cannot be completely dehydrated, but rather between about 2% and about 5% of the original water in the preparation must be left in the preparation at the end of the dehydration process. In terms of moles of water per mole of lipid, this means that between about 12 and about 35 moles water/mole lipid should be present in the dehydrated preparation.

In accordance with other dehydration protocols of the present invention, antineoplastic agents are loaded into liposomes which have previously been dehydrated for shipping, storage and the like, and then rehydrated. The dehydration is performed following the procedures discussed above, and the loading of the antineoplastic agents is performed using the transmembrane potential method described above. The transmembrane potential can be generated either before or after the dehydration step, as desired.

In addition to the foregoing methods, the invention also provides the products produced by practicing the methods. That is, it provides: 1) pharmaceutical preparations comprising an antineoplastic agent which has been loaded into liposomes by means of a transmembrane potential: 2) stabilized pharmaceutical preparations comprising an ionizable biologically-active agent encapsulated in liposomes having a transmembrane potential across their membranes so as to reduce the rate of release of the agent from the liposomes: 3) dehydrated pharmaceutical preparations comprising antineoplastic agents encapsulated in liposomes; and 4) pharmaceutical preparations comprising antineoplastic agents which have been loaded into previously dehydrated liposomes by means of a transmembrane potential.

The attainment of the foregoing and other objects and advantages of the present invention is described fully below in connection with the description of the preferred embodiments of the invention.

As used herein, the terms "pharmaceutical preparation," "ionizable antineoplastic agent," and "ionizable biologically-active agent" have the following meanings: pharmaceutical preparation means a composition of matter suitable for administration to humans or animals and comprising a biologically active material and appropriate buffers, diluents, carriers, and the like; ionizable antineoplastic agent means an antineoplastic agent which can exist in a charged state when dissolved in an aqueous medium; and ionizable biologically-active agent means a biologically-active agent which can exist in a charged state when dissolved in an aqueous medium.

DESCRIPTION OF THE PREFERRED EMBODIMENTS

Figure 1:
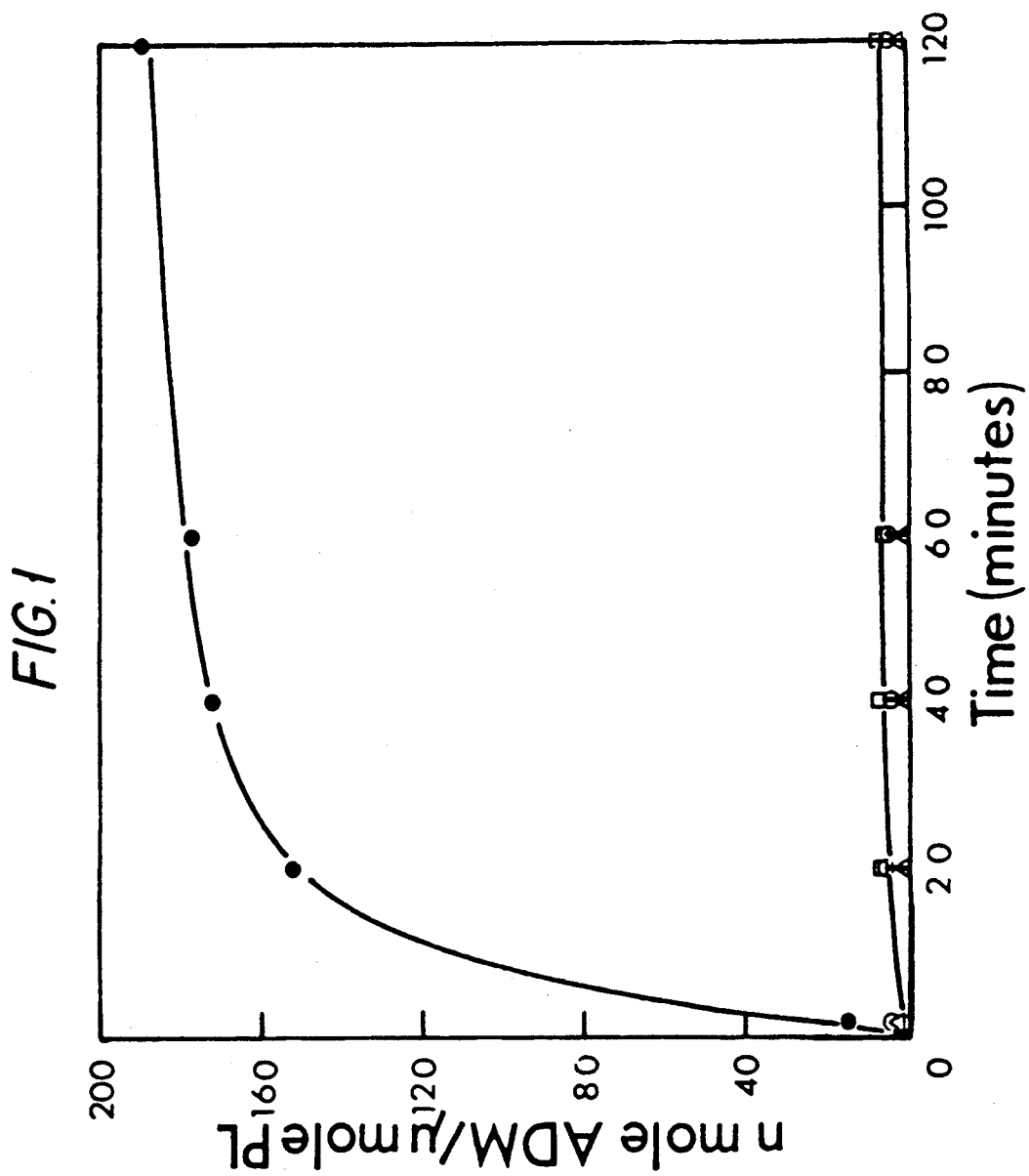
FIG. 1 shows the uptake of adriamycin (ADM) into large unilamellar vesicles (LUVs) in the presence and absence of a $Na^+/K^+$ diffusion potential. Egg-PC LUVs (1 umol phospholipid/ml) were incubated at 20° C. in the presence f 0.2 mM adriamycin. Drug uptake was quantitated as described below in Materials and Methods. Experimental conditions were as follows: open triangles—vesicles with 169 mM potassium glutamate, 20 mM Hepes (pH 7.5) in the internal and external medium; open circles—vesicles with 169 mM potassium glutamate, 20 mM Hepes (pH 7.5) in the internal and external medium plus valinomycin; open squares—vesicles having 169 mM potassium glutamate, 20 mM Hepes (pH 7.5) in the internal medium and 150 mM NaCl, 20 mM Hepes (pH 7.5) in the external medium; solid circles—vesicles having 169 mM potassium glutamate, 20 mM Hepes (pH 7.5) in the internal medium and 150 mM NaCl, 20 mM Hepes (pH 7.5) in the external medium plus valinomycin.

As described above, the present invention relates to the encapsulation of antineoplastic agents in liposomes.

The liposomes in which the antineoplastic agents are encapsulated can have a variety of compositions and internal contents, and can be in the form of multilamellar, unilamellar, or other types of liposomes or, more generally, lipid-containing particles, now known or later developed. For example, the lipid-containing particles can be in the form of steroidal liposomes, stable plurilamellar liposomes (SPLVs), monophasic vesicles (MPVs), or lipid matrix carriers (LMCs) of the types disclosed in copending and commonly assigned U.S. Pat. Applications Ser. Nos. 476,496, 521,176, 591,576 and 599,691, filed Mar. 24, 1983, Aug. 8, 1983, Mar. 20, 1984, and Apr. 12, 1984, respectively, the pertinent portions of which are incorporated herein by reference.

The liposomes can be prepared by any of the techniques now known or subsequently developed for preparing liposomes. For example, the liposomes can be formed by the conventional technique for preparing multilamellar liposomes (MLVs), that is, by depositing one or more selected lipids on the inside walls of a suitable vessel by dissolving the lipids in chloroform and then evaporating the chloroform, adding the aqueous solution which is to be encapsulated to the vessel, allowing the aqueous solution to hydrate the lipid, and swirling or vortexing the resulting lipid suspension to produce the desired liposomes.

Alternatively, techniques used for producing large unilamellar liposomes (LUVs), such as, reverse-phase evaporation, infusion procedures, and detergent dilution, can be used to produce the liposomes. A review of these and other methods for producing liposomes can be found in the text *Liposomes*, Marc J. Ostro, ed., Marcel Dekker, Inc., New York, 1983, Chapter 1, the pertinent portions of which are incorporated herein by reference. See also Szoka, Jr., et al., (1980) Ann. Rev. Biophys. Bioengr., 9:467, the pertinent portions of which are also incorporated herein by reference. A particularly preferred method for preparing LUVs is described in commonly assigned and copending U.S. Pat. Application Ser. No. 622,690, filed June 20, 1984, and entitled "Extrusion Technique for Producing Unilamellar Vesicles," the pertinent portions of which are incorporated herein by reference.

As other alternatives, the liposomes can be produced in accordance with the procedures described in U.S. Pat. Applications Ser. Nos. 476,496, 521,176 and 599,691, referred to above. Also, rather than using liposomes per se, other lipid-containing particles, such as those described in U.S. Pat. Application Ser. No. 591,576, referred to above, can be used in the practice of the present invention. Furthermore, in the case of MLVs, if desired, the liposomes can be subjected to multiple freeze-thaw cycles in liquid nitrogen (e.g., five or more cycles) to enchance their trapped volumes and trapping efficiencies and to provide a more uniform interlamellar distribution of solute. Similarly, if desired, the liposomes or lipid-containing particles which are used to carry the antineoplastic agents can be given a more uniform size distribution by subjecting them to the process of commonly assigned and copending U.S. Pat. Application Ser. No. 622,502, filed June 20, 1984, and entitled "Liposomes Having Defined Size Distributions," the pertinent portions of which are incorporated herein by reference.

As discussed above, in accordance with one of its aspects, the present invention provides a method for loading liposomes with ionizable antineoplastic agents wherein a transmembrane potential is created across the walls of the liposomes and the antineoplastic agent is loaded into the liposomes by means of the transmembrane potential. The transmembrane potential is generated by creating a concentration gradient for one or more charged species (e.g., $Na^+$, $K^+$ and/or $H^+$) across the liposome membranes. The concentration gradient is created by producing liposomes having different internal and external media, i.e., internal and external media having different concentrations of the one or more charged species.

Specifically, liposomes are prepared which encapsulate a first medium having a first concentration of the one or more charged species. For a typical liposome preparation technique (see discussion above), this first medium will surround the liposomes as they are formed, and thus the liposomes' original external medium will have the same composition as the first medium. To create the concentration gradient, the original external medium is replaced by a new external medium having a different concentration of the one or more charged species. The replacement of the external medium can be accomplished by various techniques, such as, by passing the liposome preparation through a gel filtration column, e.g., a Sephadex column, which has been equilibrated with the new medium, or by centrifugation, dialysis, or related techniques.

Depending upon the permeability of the liposome membranes, the full transmembrane potential corresponding to the concentration gradient will either form spontaneously or a permeability enhancing agent, e.g., an ionophore, such as, valinomycin, may have to be added to the bathing medium. (Note that, if desired, the permeability enhancing agent can be removed from the preparation after loading has been completed using chromatography or other techniques.) In either case, a transmembrane potential having a magnitude defined by the Nernst equation will appear across the liposomes' membranes.

In accordance with the invention, it has been found that this transmembrane potential can be used to load ionizable antineoplastic agents into the liposomes. Specifically, once liposomes having a concentration gradient and thus a transmembrane potential of the appropriate orientation have been prepared, the process of loading antineoplastic agents into the liposomes reduces to the very simple step of adding the agent to the external medium. Once added, the transmembrane potential will automatically load the agent into the liposomes. Moreover, as described in detail in Example 1 below, the loading is not only simple, but is also extremely efficient. As described in that example, it has been found that trapping efficiencies for antineoplastic agents of 95% and higher can be readily achieved with the transmembrane potential loading technique.

The transmembrane potential loading method can be used with essentially any antineoplastic agent which can exist in a charged state when dissolved in an appropriate aqueous medium (e.g., organic compounds which include an amino group which can be protonated). Preferably, the agent should be relatively lipophilic so that it will partition into the liposome membranes. Examples of some of the antineoplastic agents which can be loaded into liposomes by this method include doxorubicin, mitomycin, bleomycin, daunorubicin, streptozocin, vinblastine, vincristine, mechlorethamine hydrochloride, melphalan, cyclophosphamide, triethylenethiophosphoramide, carmustine, lomustine, semustine, fluorouracil, hydroxyurea, thioguanine, cytarabine, floxuridine, decarbazine, cisplatin and procarbazine.

In addition to loading a single antineoplastic agent, the method can be used to load multiple antineoplastic agents, either simultaneously or sequentially. Also, the liposomes into which the ionizable antineoplastic agents are loaded can themselves be pre-loaded with other antineoplastic agents or other drugs using conventional encapsulation techniques (e.g., by incorporating the drug in the buffer from which the liposomes are made). Since the conventionally loaded materials need not be ionizable, this approach provides great flexibility in preparing liposome-encapsulated "drug cocktails" for use in cancer therapies. Indeed, essentially all types of anti-cancer drugs can be pre-loaded, at least to some extent, in either the lipid or aqueous portion of the liposomes. Of course, if desired, one or more of the ionizable drugs listed above can be pre-loaded and then the same or a different drug added to the liposomes using the transmembrane potential approach.

Turning now to the aspects of the invention relating to reducing the rate of release of an ionizable antineoplastic agent or other ionizable biologically-active agent drug from liposomes, it has been surprisingly found that the rate of release can be markedly reduced by creating a transmembrane potential across the liposome membranes which is oriented to retain the agent in the liposomes. That is, for an agent which is positively charged when ionized, a transmembrane potential is created across the liposome membranes which has an inside potential which is negative relative to the outside potential, while for a agent which is negatively charged, the opposite orientation is used.

As with the transmembrane loading aspects of the invention, the transmembrane potentials used to reduce the rate of drug release are created by adjusting the concentrations on the inside and outside of the liposomes of a charged species such as $Na^+$, $K^+$ and/or $H^+$. Indeed, if the liposomes have been loaded by means of a transmembrane potential produced by such a concentration gradient, simply keeping the liposomes in an external medium which will maintain the original concentration gradient will produce the desired reduction in the rate of release. Alternatively, if a transmembrane potential has not already been created across the liposome membranes, e.g., if the liposomes have been loaded using a conventional technique, the desired transmembrane potential can be readily created by changing the composition of the external medium using the exchange techniques described above.

The reduced rate of release aspect of the invention can be used with essentially any ionizable biologically-active agent which can be encapsulated in a liposome. In particular, the technique can be used with the ionizable antineoplastic agents listed above and with a variety of other ionizable drugs, including such drugs as local anesthetics, e.g., dibucaine and chlorpronazine; beta-adrenergic blockers, e.g., propanolol, timolol and labetolol; antihypertensive agents, e.g., clonidine, and hydralazine; anti-depressants, e.g., imipramine, amiriptyline and doxepim; anti-convulsants, e.g., phenytoin; anti-emetics, e.g., procainamide and prochlorperazine: antihistamines, e.g., diphenhydramine, chlorpheniramine and promethazine; anti-arrhythmic agents, e.g., quinidine and disopyramide; anti-malarial agents, e.g., chloroquine; and analgesics e.g., cocaine. In general, the largest reductions in the rate of release will be seen for lipophilic materials since their normal rates of release are typically higher than those of non-lipophilic materials.

Turning next to the aspects of the invention relating to the dehydration protocols, two basic approaches are provided: 1) the liposomes can be loaded with antineoplastic agents (e.g., using conventional techniques or the transmembrane potential loading technique described above), dehydrated for purposes of storage, shipping, and the like, and then rehydrated at the time of use; or 2) pre-formed liposomes can be dehydrated for storage, etc., and then at or near the time of use, they can be rehydrated and loaded with an ionizable antineoplastic agent using the transmembrane potential loading technique described above.

In either case, the liposomes are preferably dehydrated using standard freeze-drying equipment or equivalent apparatus, that is, they are preferably dehydrated under reduced pressure. If desired, the liposomes and their surrounding medium can be frozen in liquid nitrogen before being dehydrated. Alternatively, the liposomes can be dehydrated without prior freezing, by simply being placed under reduced pressure. Dehydration without prior freezing takes longer than dehydration with prior freezing, but the overall process is gentler without the freezing step, and thus there is in general less damage to the liposomes and a corresponding smaller loss of the internal contents of the liposomes. Dehydration without prior freezing at room temperature and at a reduced pressure provided by a vacuum pump capable of producing a pressure on the order of 1 mm of mercury typically takes between approximately 24 and 36 hours, while dehydration with prior freezing under the same conditions generally takes between approximately 12 and 24 hours.

So that the liposomes will survive the dehydration process without losing a substantial portion of their internal contents, it is important that one or more protective sugars be available to interact with the liposome membranes and keep them intact as the water in the system is removed. A variety of sugars can be used, including such sugars as trehalose, maltose, sucrose, glucose, lactose, and dextran. In general, disaccharide sugars have been found to work better than monosaccharide sugars, with the disaccharide sugars trehalose and sucrose being most effective. Other more complicated sugars can also be used. For example, aminoglycosides, including streptomycin and dihydrostreptomycin, have been found to protect liposomes during dehydration.

The one or more sugars are included as part of either the internal or external media of the liposomes. Most preferably, the sugars are included in both the internal and external media so that they can interact with both the inside and outside surfaces of the liposomes' membranes. Inclusion in the internal medium is accomplished by adding the sugar or sugars to the buffer which becomes encapsulated in the liposomes during the liposome formation process. Since in most cases this buffer also forms the bathing medium for the finished liposomes, inclusion of the sugars in the buffer also makes them part of the external medium. Of course, if an external medium other than the original buffer is used, e.g., to create a transmembrane potential (see above), the new external medium should also include one or more of the protective sugars.

The amount of sugar to be used depends on the type of sugar used and the characteristics of the liposomes to be protected. As described in commonly assigned and copending U.S. Pat. Application Ser. No. 638,809, filed Aug. 8, 1984, and entitled "Dehydrated Liposomes," the pertinent portions of which are incorporated herein by reference, persons skilled in the art can readily test various sugar types and concentrations to determine which combination works best for a particular liposome preparation. In general, sugar concentrations on the order of 100 mM and above have been found necessary to achieve the highest levels of protection. In terms of moles of membrane phospholipid, millimolar levels on the order of 100 mM correspond to approximately 5 moles of sugar per mole of phospholipid.

In the case of dehydration without prior freezing, if the liposomes being dehydrated are of the type which have multiple lipid layers and if the dehydration is carried to an end point where between about 2% and about 5% of the original water in the preparation is left in the preparation, the use of one or more protective sugars may be omitted.

Once the liposomes have been dehydrated, they can be stored for extended periods of time until they are to be used. The appropriate temperature for storage will depend on the make up of the liposomes and the temperature sensitivity of whatever materials have been encapsulated in the liposomes. For example, as is known in the art, various antineoplastic agents are heat labile, and thus dehydrated liposomes containing such agents should be stored under refrigerated conditions so that the potency of the agent is not lost. Also, for such agents, the dehydration process is preferably carried out at reduced temperatures, rather than at room temperature.

When the dehydrated liposomes are to be used, rehydration is accomplished by simply adding an aqueous solution, e.g., distilled water or an appropriate buffer, to the liposomes and allowing them to rehydrate. The liposomes can be resuspended into the aqueous solution by gentle swirling of the solution. The rehydration can be performed at room temperature or at other temperatures appropriate to the composition of the liposomes and their internal contents.

If the antineoplastic agent which is to be administered was incorporated into the liposomes prior to dehydration, and no further composition changes are desired, the rehydrated liposomes can be used directly in the cancer therapy following known procedures for administering liposome encapsulated drugs.

Alternatively, using the transmembrane potential procedures described above, ionizable antineoplastic agents can be incorporated into the rehydrated liposomes just prior to administration. In connection with this approach, the concentration gradient used to generate the transmembrane potential can be created either before dehydration or after rehydration using the external medium exchange techniques described above.

For example, liposomes having the same internal and external media, i.e., no transmembrane potentials, can be prepared, dehydrated, stored, rehydrated, and then the external medium can be replaced with a new medium having a composition which will generate transmembrane potentials, and the transmembrane potentials used to load ionizable antineoplastic agents into the liposomes. Alternatively, liposomes having internal and external media which will produce transmembrane potentials can be prepared, dehydrated, stored, rehydrated, and then loaded using the transmembrane potentials.

Without intending to limit it in any manner, the present invention will be more fully described by the following examples. The materials and methods which are common to the various examples are as follows.

MATERIALS AND METHODS

Materials

Egg phosphatidylcholine (egg-PC or EPC) was isolated employing standard procedures (see, for example, Singleton, et al., (1965) Journal of the American Oil Chemical Society, 42:53) and was more than 99% pure as determined by TLC. Egg PS was prepared from egg-PC as described in Hope, et al., (1985), Biochim. Biophys. Acta 812:55.

Cholesterol, valinomycin, vinblastine, Hepes, dipalmitoylphosphatidylcholine (DPPC), trehalose, CCCP, and salts were obtained from the Sigma Chemical Company (St. Louis, Mo.).

Adriamycin was obtained either from Adria Laboratory (Mississauga, Ontario) or from the Cancer Research Centre (Vancouver, B.C.). Methotrexate and cytosine arabinoside were also obtained from the Cancer Research Centre.

Tritiated methotrexate, DPPC and methyltriphenylphosphonium, as well as $^{22}Na^+$, $^3H$-inulin, $^-C$-inulin, $^3H$-tetraphenylphosphonium bromide and $^3H$-$H_2O$ were obtained from New England Nuclear (Lachine, Quebec). Tritiated cytosine arabinoside was obtained from Amersham (Oakville, Ontario).

Reagents

Potassium glutamate, KCl and NaCl buffers were prepared in a 20 mM Hepes buffer adjusted to pH 7.5 with NaOH. The solutions were adjusted to a common osmolarity of 310 mOsm/kg, which corresponded to KCl, NaCl and potassium glutamate concentrations of 150, 150 and 169 mM, respectively.

Vesicle Preparation

Vesicles were prepared using the extrusion techniques described in U.S. Pat. Applications Ser. Nos. 622,690 and 622,502, referred to above. A complete description of the techniques used appears in those applications and is incorporated herein by reference. The technique is also described in Hope, et al., (1985) Biochim. Biophys. Acta, 812:55-65. Vesicles prepared by these techniques will be referred to herein as either ETVs, i.e, Extrusion Technique Vesicles or LUVs, i.e., Large Unilamellar Liposomes.

Briefly, dry lipid films were hydrated with the appropriate buffers to produce large multilamellar vesicles at concentrations ranging between 25 and 200 umol phospholipid/ml. Where used, $^{22}Na^+$(5 uCi) or $^3H$-inulin (5 uCi) was added to the dry lipid prior to hydration.

The mixture was dispersed by vortexing and then passed ten times through two stacked polycarbonate filters of 100 nm pore size (Nuclepore, Inc., Pleasanton, CA) using a pressure of, for example, 250 psi. For the experiments of Examples 1B and 2B, the dispersions were frozen in liquid nitrogen and thawed 5 times prior to extrusion through the polycarbonate filters. The resulting vesicles had an average diameter of 103 nm and a trapped volume of approximately 1.5 ul/umol phospholipid. For the remaining experiments of Examples 1 and 2, the initial extrusion was followed by two freeze-thaw cycles in liquid nitrogen, after which the vesicles were passed through the filters five more times. In this case, the vesicles had an average diameter of 90 nm and a trapped volume of again approximately 1.5 ul/umol phospholipid.

Unencapsulated $^{22}Na^+$ or $^3H$-inulin was removed by passing the vesicles through a column (1.4×10 cm) of either Sephadex G-50 for removal of $^{22}Na^+$ or Ultragel AcA 34 for removal of $^3H$-inulin. This procedure generally diluted the phospholipid content of the sample by approximately 50%.

Dehydration

Samples (1 ml) were dried in 10 ml Kimex tubes at room temperature under high vacuum using a Virtis Freeze Drier (Gardiner, N.Y.). In some cases, the samples were frozen in liquid nitrogen prior to dehydration. In either case, the reduced pressure dehydration process was carried out for approximately 24 hours.

Rehydration

Following dehydration and storage for periods ranging from 1 to 7 days, the samples were rehydrated with distilled water (900 ul) and the vesicles dispersed by gentle vortexing.

Assays

Phospholipids were quantified by determination of inorganic phosphorus as described by Chen, et al., (1956) Anal. Chem. 28:1756. See also Bottcher, et al., (1961) Anal. Chima. Acta, 24203. Alternatively, in some cases, liquid scintillation counting to quantitate [$^3H$]DPPC (0.05 uCi/umol lipid) was performed.

Adriamycin was quantitated by mixing an aliquot of the vesicle suspension with 0.5% Triton X-100 (which disrupted the vesicles and released the trapped drug) and monitoring the absorbance at 480 nm employing a Pye Unicam SP8-200 spectrophotometer. Vinblastine was assayed by determining the absorbance at 265 nm of the suspension dissolved in 94% ethanol.

The various tritiated compounds and $^{14}C$-inulin were counted in a Phillips PW 4700 liquid scintillation counter, while $^{22}Na^+$ was quantified by gamma counting on a Beckman Gamma 800.

EXAMPLE 1

Loading of Ionizable Antineoplastic Agents Into Liposomes Using Transmembrane Potentials This example illustrates the active loading of ionizable antineoplastic agents into liposomes using transmembrane potentials.

Part A of the example illustrates the loading of the anti-cancer drugs adriamycin and vinblastine into liposomes using a $Na^+/K^+$ gradient to generate transmembrane potentials; Part B illustrates the loading of adriamycin using a pH gradient; and Part C illustrates the use of transmembrane potentials to load adriamycin into liposomes which previously have been passively loaded with either methotrexate or cytosine arabinoside.

Part A

Active Loading Using Na+/K+ Gradients

Membrane potentials were generated by forming egg-PC LUVs in the potassium glutamate buffer (described above) and subsequently exchanging the untrapped buffer for the NaCl buffer (described above) employing Sephadex G-50 desalting columns. Where employed, the potassium ionophore, valinomycin (1 mg/ml ethanol), was added to achieve a concentration of 0.5 ug per umol lipid. Membrane potentials were determined using the membrane potential probe methyltriphenylphosphonium (see Bally, et al., (1985), Biochim. Biophys. Acta, 812:66; see also Example 4, infra, where the probe tetraphenylphosphonium rather than methyltriphenylphosphonium is used).

Adriamycin (0.2 mM final concentration) and vinblastine (0.2 mM final concentration) were added to LUV dispersions with and without Na+/K+ ion gradients and with and without valinomycin. At various times, the non-sequestered drug was removed by passing aliquots of the solution, over 1 ml Sephadex G-50 columns. Lipid and drug concentrations were then assayed using the procedures described above. The results are shown in FIGS. 1 and 2.

As shown in FIG. 1, in the absence of both a Na+/K+ gradient and valinomycin, low LUV-associated adriamycin levels (less than 6 nmol adriamycin/umol phospholipid) are observed over the 2 hour incubation period. However, in the presence of valinomycin and the Na+/K+ gradient, a remarkable increase in the amount of vesicle-associated adriamycin is observed. This uptake is more than 75% complete within 20 minutes and reaches an equilibrium level of 190 nmol adriamycin/umol phospholipid. This indicates that 95% of the drug initially contained in the solution is taken up by the vesicles, reflecting a corresponding trapping efficiency of 95%. In terms of concentrations, this uptake corresponding to an internal adriamycin concentration of approximately 127 mM.

Figure 2:
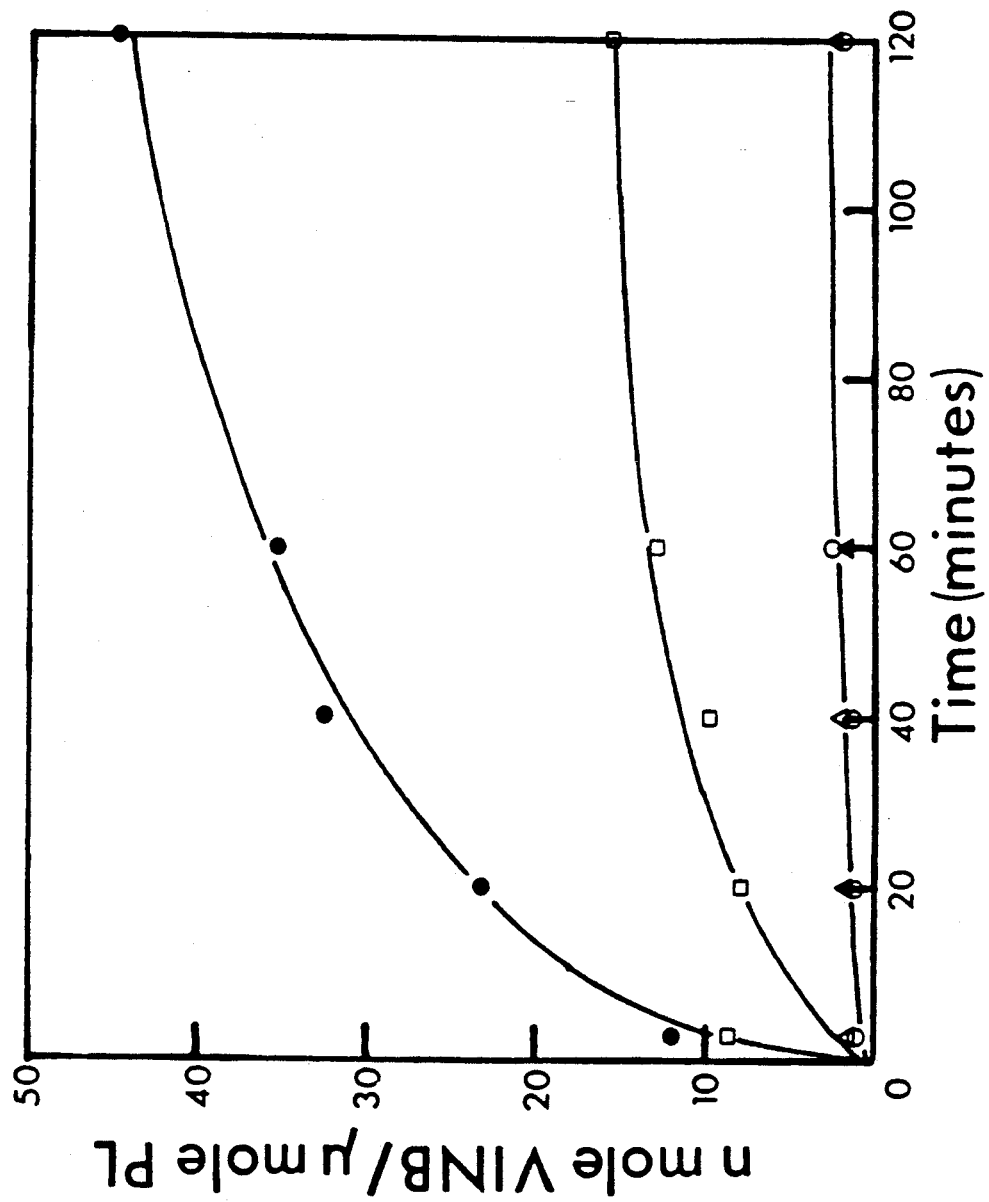
FIG. 2 shows the uptake of vinblastine (VINB) into large unilamellar vesicles in the presence and absence of a $Na^+/K^+$ diffusion potential. Egg-PC LUVs (1 umol phospholipid/ml) were incubated at 20° C. in the presence of 0.2 mM vinblastine under the following conditions: open triangles—169 mM potassium glutamate, 20 mM Hepes (pH 7.5) as the interior and exterior buffers: open circles—169 mM potassium glutamate, 20 mM Hepes (pH 7.5) as the interior and exterior buffers plus valinomycin; open squares—150 mM NaCl, 20 mM Hepes (pH 7.5) in the exterior medium and 169 mM potassium glutamate in the vesicle interior: solid circles—150 mM NaCl, 20 mM Hepes (pH 7.5) in the exterior medium and 169 mM potassium glutamate in the vesicle interior plus valinomycin.

As shown in FIG. 2, vinblastine can also be accumulated into LUV systems in response to a membrane potential. In the presence of valinomycin and a Na+/K+ gradient, 40 nmol vinblastine/umol phospholipid is accumulated within 2 hours, as compared to little or no uptake in the absence of a Na+/K+ gradient. In addition, appreciable uptake is obtained in the presence of a Na+/K+ gradient even in the absence of valinomycin.

In sum, the results of FIGS. 1 and 2 reveal a remarkable ability of LUV systems to sequester adriamycin and vinblastine in response to transmembrane potentials. Under the conditions employed, the uptake levels achieved correspond to final transmembrane drug concentration gradients of $2 \times 10^2$ and $2 \times 10^4$ for vinblastine and adriamycin, respectively. Furthermore, these gradients were found to be stable for 48 hours or longer at 20° C.

Although not wishing to be bound by any particular theory of operation, one of the mechanisms involved in the observed uptake of adriamycin, vinblastine, and other ionizable antineoplastic agents in response to a Na+/K+ gradient may involve the pH gradient which is automatically generated in response to the Na+/K+ gradient due to the permeability of liposome membranes to H+ ions. In accordance with this mechanism, the ionizable antineoplastic agent passes through the membrane in an uncharged state, with its internal and external concentrations being a function of the internal and external H+ ion concentrations, the internal concentration of the agent being high when the internal H+ concentration is high, and vice versa.

Figure 3:
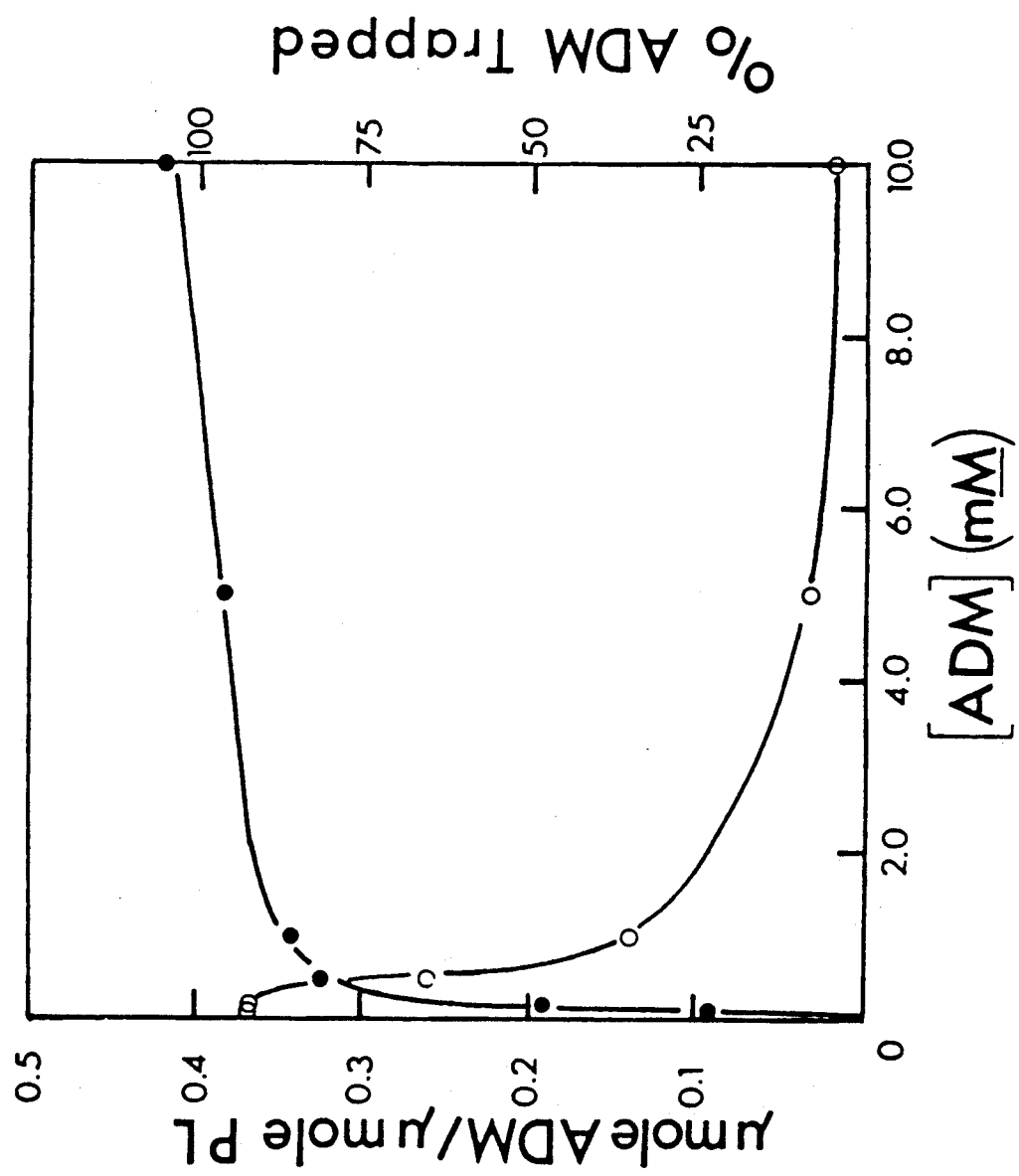
FIG. 3 shows the uptake of adriamycin (ADM) into egg-PC LUVs having $Na^+/K^+$ gradients across their membranes as a function of the initial free adriamycin concentration (solid circles). The open circles show the percentage of the total available drug which was accumulated. The vesicles (1 mM phospholipid) were incubated at 20° C. with the indicated concentrations of adriamycin for 2 hours in the presence of valinomycin.

The efficiency of the transmembrane potential loading process was further characterized by varying the amount of drug available. As shown in FIG. 3, increasing the initial adriamycin concentration from 0 to 10 mM, while maintaining a fixed vesicle concentration (1 mM phospholipid), revealed that the transmembrane potential driven adriamycin uptake process saturated at approximately 400 nmol adriamycin/umol phospholipid. Between 0 and 0.2 mM adriamycin, the uptake was proportional to the initial free concentration and was nearly quantitative (95% or higher trapping efficiencies). Above 0.2 mM adriamycin, the trapping efficiency was reduced due to the saturation of the uptake process. However, high trapping efficiencies at these higher drug concentrations could be readily achieved by the simple expedient of increasing the vesicle concentration. For example, it was found that incubation of 10 mM adriamycin in the presence of LUVs corresponding to a 50 mM phospholipid concentration yielded uptake levels of 196 nmol adriamycin/umol phospholipid, corresponding to a 98% trapping efficiency.

Similar studies employing vinblastine revealed that uptake levels saturated at 40 nmol vinblastine/umol phospholipid. Trapping efficiencies approaching 100% could be achieved on incubation of 0.2 mM vinblastine with a concentration of LUVs corresponding to 5 mM phospholipid.

Figure 4:
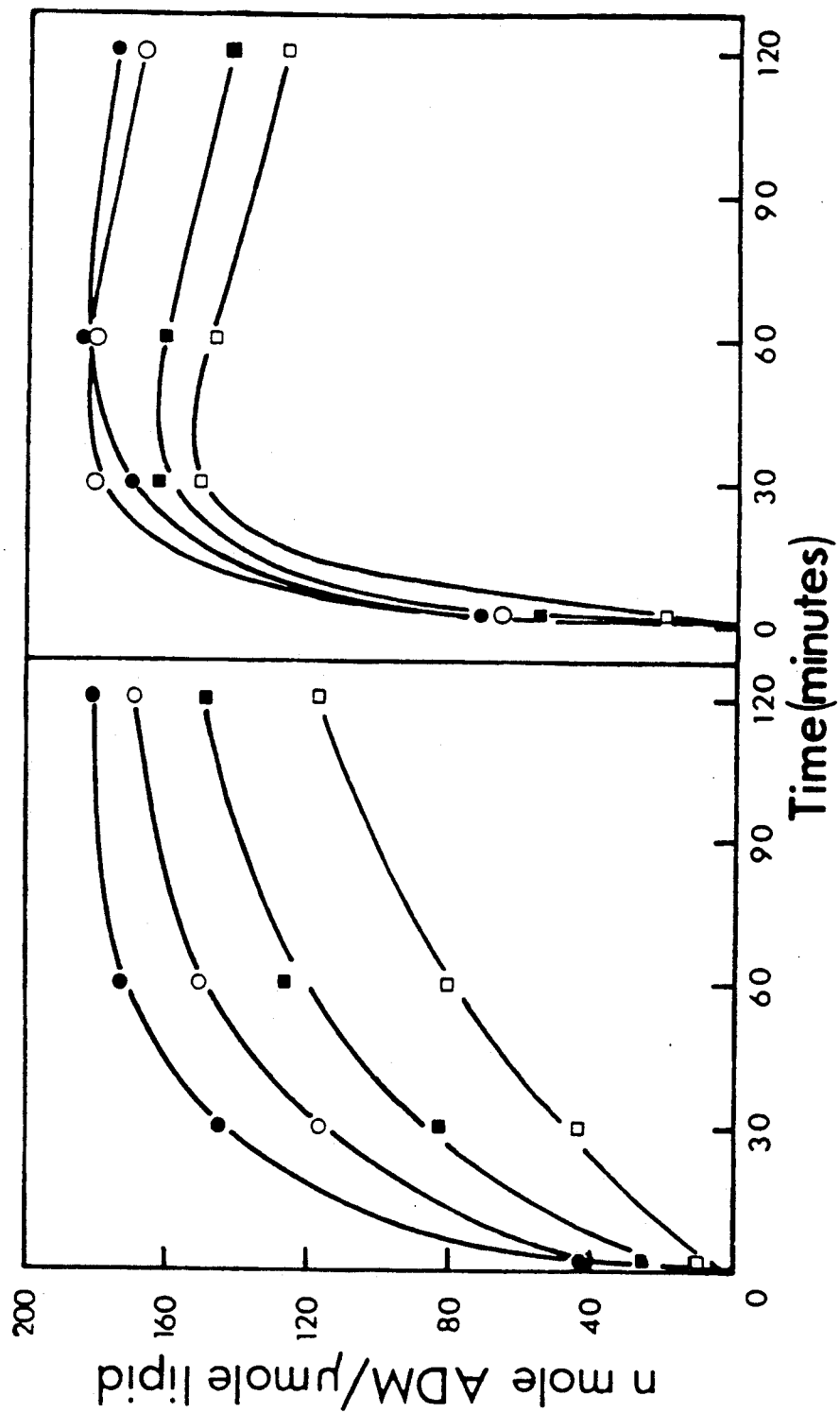
FIG. 4B shows the uptake of adriamycin (ADM) into egg-PC-cholesterol LUV systems in the presence of $Na^+/K^+$ transmembrane chemical gradients and valinomycin at (A) 20° C. and (B) 37° C. The vesicles (1 umol total lipid/ml) were incubated at 20° C. or 37° C. for 2 hours in the presence of 0.2 mM adriamycin. The molar ratios of egg-PC to cholesterol employed were: solid circles—1:0; open circles—9:1; solid squares—3:1; and open squares—1:1.

Since liposomal drug delivery systems commonly contain equimolar levels of cholesterol and more saturated phospholipid to reduce leakage of entrapped material induced by serum components (see, for example, Gabizon, et al., (1982), Cancer Res., 42:4734; Mayhew, et al., (1979), Cancer Treat. Rep., 63:1923; and Papahadjopoulos, et al., (1980), Liposomes and Immunology (Tom and Six, eds.), Elsevier, New York), an investigation was performed to determine the influence of cholesterol on active trapping of adriamycin into egg/PC LUV systems. As shown in FIG. 4A, at 20° C., a stepwise increase in cholesterol content to achieve equimolar egg-PC/cholesterol levels resulted in a corresponding decrease in the rate of adriamycin accumulation. Rapid uptake, however, still could be achieved by simply incubating the vesicle-drug system at higher temperatures. As shown in FIG. 4B, equilibrium uptake levels are achieved within 30 minutes at 37° C. This effect was most pronounced for the egg-PC/cholesterol (1:1) system, where increasing the temperature from 20° C. to 37° C. resulted in an increase of vesicle-associated adriamycin from 42 to 153 nmol/umol lipid after a 30 minute incubation. These results indicate that it is important to have a rather "fluid" bilayer for efficient transport of drugs into the vesicle interior.

Figure 5:
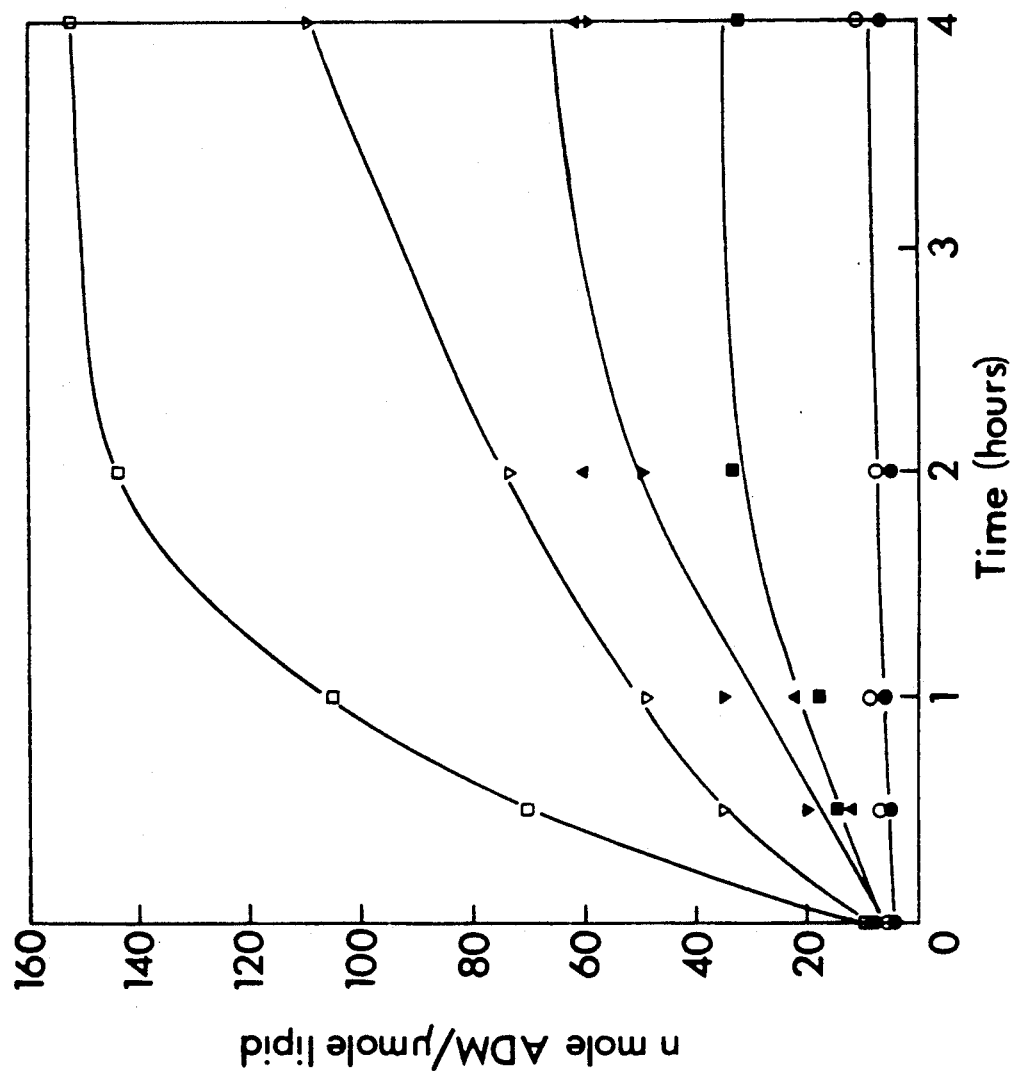
FIG. 5 shows the uptake of adriamycin (ADM) into DPPC-cholesterol (1:1) LUVs (1 mM lipid) in the presence of $Na^+/K^+$ transmembrane chemical gradients after incubations in the presence of 0.2 mM adriamycin at various temperatures: open circles—20° C., in the presence of valinomycin; solid squares—37° C., in the presence of valinomycin; solid circles—37° C., in the absence of valinomycin; open squares—60° C., in the presence of valinomycin; solid downward facing triangles—60° C., in the absence of valinomycin: solid upward facing triangles—Egg-PC LUVs (1 mM) at 37° C., in the absence of valinomycin; open downward facing triangles—Egg-PC LUVs at 60° C., in the absence of valinomycin.

The effects of increased saturation of the phospholipid acyl chains on transmembrane potential loading of adriamycin were examined by monitoring uptake into DPPC-cholesterol (1:1) LUVs. As shown in FIG. 5, no uptake of adriamycin could be observed over 4 hours at 20° C. However, incubation at 60° C. resulted in sequestered adriamycin levels of 150 nmol drug/umol lipid within 2 hours. Further, significant uptake (to approximately 60 nmol/umol lipid) was observed for these systems incubated in the absence of valinomycin. Similarly, for egg-PC LUVs, adriamycin uptake levels of 60 and 100 nmol drug/umol lipid at 37° C. and 60° C., respectively, were achieved in the absence of valinomycin (FIG. 5).

Figure 6:
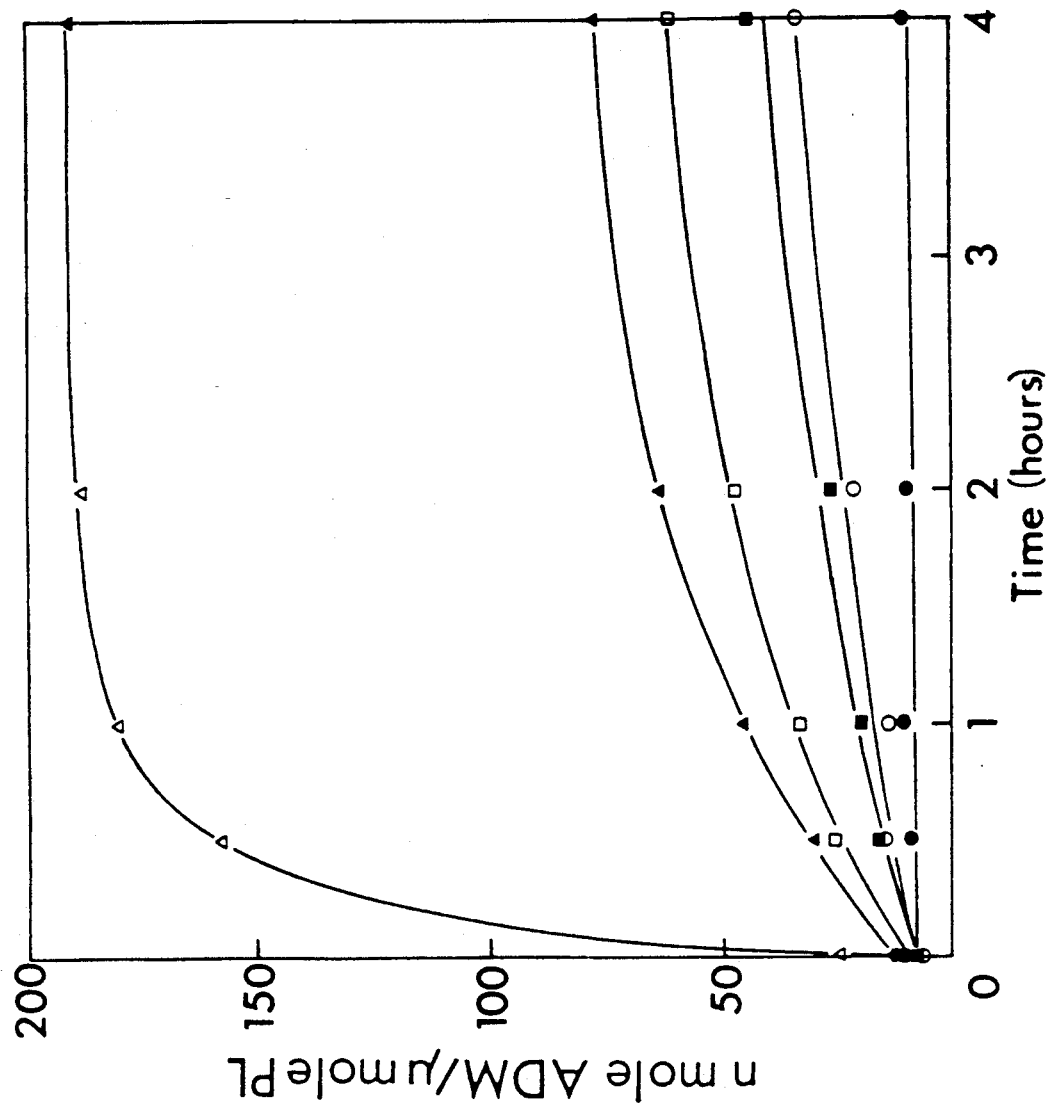
FIG. 6 shows the uptake of adriamycin (ADM) into egg-PC/egg-PS LUVs in the presence of $Na^+/K^+$ chemical gradients after incubation at 20° C. in the presence of 0.2 mM adriamycin: open triangles—egg-PC/egg-PS (4:1), in the absence of valinomycin; solid triangles —egg-PC/egg-PS (4:1), in the absence of valinomycin; open squares—egg-PC/egg-PS (9:1), in the absence of valinomycin; solid squares—egg-PC/egg-PS (20:1), in the absence of valinomycin; open circles—egg-PC/egg-PS (50:1), in the absence of valinomycin; solid circles—uptake into the egg-PC/egg-PS (4:1) system in the absence of an $Na^+/K^+$ gradient ($K^+$ buffer inside and out).

In addition to variations in acyl chain composition and cholesterol content, charged lipid species, which influence in vivo distribution and uptake processes, have also been incorporated into liposomal delivery systems. See, for example, Fraley, et al., (1981), Biochemistry, 20:6978: Jonah, et al., (1975), Biochim. Biophys. Acta, 401:336; and Mauk, et al., (1979), Proc. Natl. Acad. Sci. USA, 76:765. In order to demonstrate that transmembrane potential loading can used with such systems, the effects of the acidic (negatively charged) phospholipid, egg-PS, on transmembrane potential loading of adriamycin into egg-PC LUVs was examined. As shown in FIG. 6, systems containing 20 mol% egg-PS exhibited drug uptake behavior in the presence of valinomycin which was virtually identical to that observed in the absence of egg-PS (FIG. 1). However, in contrast to the pure egg-PC systems, significant uptake was observed in egg-PS containing LUVs in the absence of valinomycin. Increasing the egg-PS content from 2 to 20 mol% increased such uptake (2 hour incubation) from 30 to 78 nmol adriamycin-/umol phospholipid.

Part B

Active Loading Using pH Gradients

Transmembrane pH gradients were generated by forming LUVs in 150 mM KOH, 175 mM glutamic acid (pH 4.6) and subsequently exchanging the untrapped buffer for 150 mM KOH, 125 mM glutamic acid, 30 mM NaCl (pH 7.5) employing Sephadex G-50 desalting columns (Hope, et. al., (1985), Biochim. Biophys. Acta, 812:55). Where employed, the proton ionophore CCCP (10 mM in ethanol) was added to achieve a concentration of 10 uM.

Adriamycin (0.2 mM final concentration) was added to the LUV dispersions. At various times, the nonsequestered drug was removed by passing aliquots of the solution over 1 ml Sephadex G-50 columns. Lipid and drug concentration were then assayed.

Figure 7A:
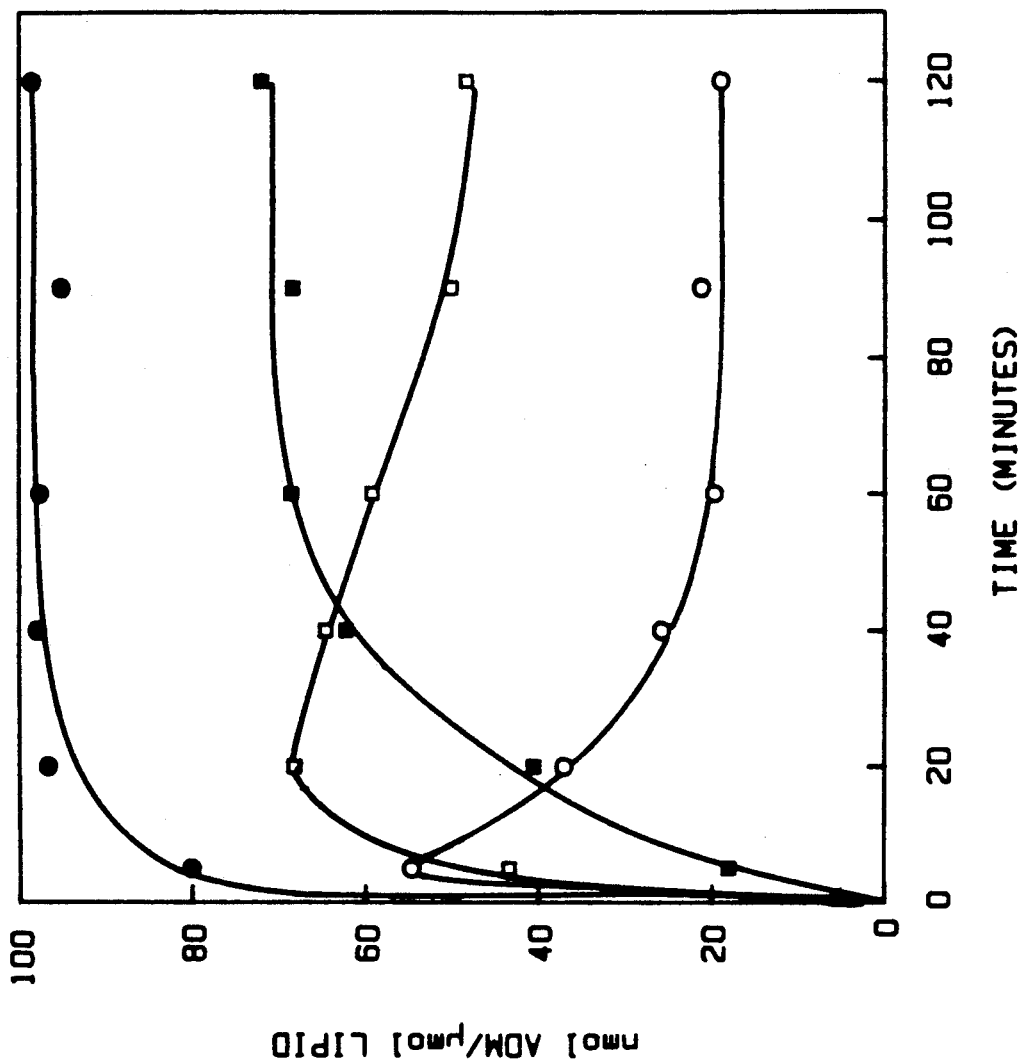
FIG. 7B shows the uptake of adriamycin into LUVs exhibiting a transmembrane pH gradient at 20° C. (A) and 37° C. (B). Experimental conditions were: 2 mM lipid, 0.2 mM adriamycin in the absence (solid symbols) and presence (open symbols) of the proton ionophore CCCP (10 uM). The interior buffer composition was 150 mM KOH, 175 mM glutamic acid (pH 4.6), whereas the exterior buffer composition consisted of 150 mM KOH, 125 mM glutamic acid, 30 mM NaCl (pH 7.5). Lipid compositions were EPC (circles) and EPC/cholesterol at a molar ratio of 1:1 (squares).

FIG. 7 demonstrates that LUVs composed of EPC and EPC/cholesterol (1:1) displaying a transmembrane pH gradient actively accumulate adriamycin in the absence of the proton ionophore CCCP. At 20° C., 50 percent of maximum uptake was observed at 15 minutes and less than 5 minutes for the EPC/cholesterol and the EPC LUVs, respectively (FIG. 7A). These results are consistent with the relative proton permeabilities of the two membrane systems. The percent trapping efficiencies observed for the EPC and EPC/cholesterol vesicles were 98 and 72 percent, respectively, comparable to values reported above for the Na+/K+ gradients. The slightly lower amount of uptake obtained for the cholesterol containing LUVs may be due to the fact that these vesicles exhibit slightly lower trapped volume values than do EPC vesicles.

Inclusion of CCCP in the incubation mixture resulted in transient high level accumulation of adriamycin followed by a gradual release of the drug from the vesicle interior. Since the LUV systems are apparently sufficiently permeable to protons to accumulate adriamycin in the absence of CCCP, it is likely that addition of the ionophore breaks down the pH gradient thus eliminating the energetic force maintaining the very large transmembrane drug concentration gradient.

Figure 7B:
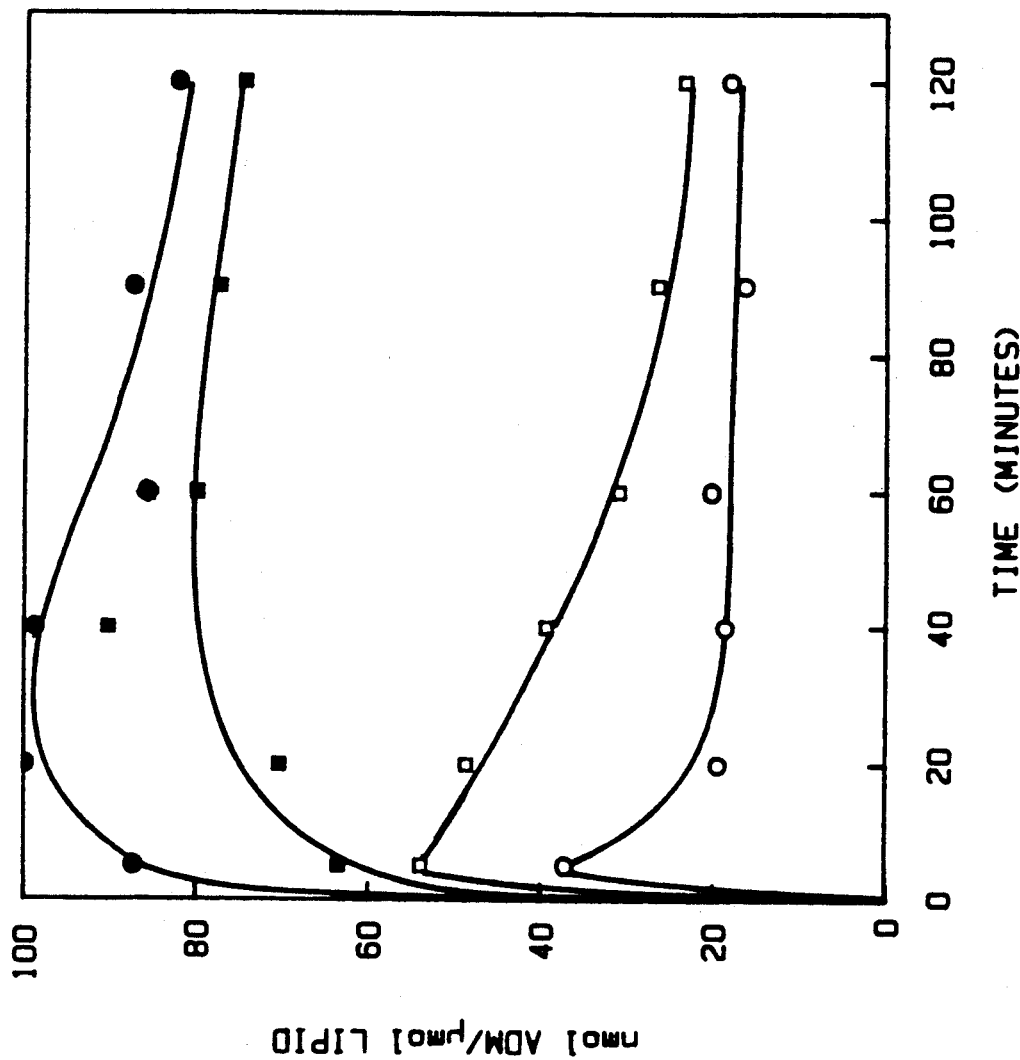

Increasing the incubation temperature to 37° C. increased the rate of uptake for EPC/cholesterol LUVs (FIG. 7B) as compared to systems equilibrated at 20° C. (FIG. 7B). A slow release of adriamycin after 20 minutes was observed for EPC vesicles at elevated temperatures in the absence of CCCP, while rapid release occurred when the ionophore was present. Again, these results correspond to the relative proton permeabilities for the various LUV systems.

Part C

Active/Passive Loading—"Drug Cocktails"

The water-soluble anticancer drugs, methotrexate and cytosine arabinoside, which do not exhibit lipophilic or cationic characteristics, were passively encapsulated in LUVs during the initial vesicle formation process.

Briefly, egg-PC LUVs (187 umol phospholipid/ml) were generated in the potassium glutamate buffer described above to which had been added 20 mg/ml cytosine arabinoside (2 uCi/ml [$^3$H]cytosine arabinoside) or 10 mg/ml methotrexate (2 uCi/ml [$^3$H]methotrexate). The vesicles were subsequently passed over a gel filtration column pre-equilibrated with the NaCl buffer described above, which removed untrapped drug and also established a Na+/K+chemical gradient. Analysis of LUVs prepared in this manner revealed that 33% of the available cytosine arabinoside or methotrexate was encapsulated (see Table I).

Following the passive trapping of the methotrexate and cytosine arabinoside, adriamycin was actively loaded into the vesicles employing the Na+/K+ gradient and valinomycin. In particular, as shown in Table I, incubation of an aliquot of the vesicles (1.0 mM phospholipid) in the presence of 0.2 mM adriamycin resulted in the uptake of 98% of the available adriamycin. Trapping efficiencies and uptake levels observed for adriamycin were almost identical to those observed in the absence of passively trapped drug (compare Table I and FIGS. 1 and 2).

EXAMPLE 2

Reduction in the Rate of Release of Charged Drugs From Liposomes Using Transmembrane Potentials This example illustrates the ability of a transmembrane potential to reduce the rate at which ionizable drugs are released from liposomes. Parts A and B of the example illustrate, respectively, the use of Na+/K+ gradients and pH gradients to generate the requisite transmembrane potentials.

Part A

Use of Na+/K+Gradients to Reduce Drug Release Rates

The rate of release of adriamycin from LUVs subsequent to active trapping following the procedures of Example 1; A was assayed as follows vesicles (10 mM phospholipid) containing adriamycin were first passed over a 15 ml gel filtration column equilibrated with either the NaCl or KCl buffers, described above, to remove free drug. The eluate was then placed in a flow dialysis apparatus equilibrated at 37° C. Flow rates were adjusted to achieve total exchange of the sample compartment volume (50 ml) in 20 minutes or less. Aliquots (100 ul) were removed at various times and untrapped material was separated employing 1 ml gel filtration columns. The sample was then assayed for adriamycin and phospholipid.

The results of these experiments are shown in Table II. As shown therein, the presence of a Na$^+$/K$^+$ transmembrane gradient resulted in significantly longer drug retention times for egg-PC, egg-PC/egg-PS (8:2), and egg-PC/cholesterol (1:1) vesicles. Similar experiments were run with DPPC/cholesterol (1:1) vesicles. In this case, complex drug release kinetics were observed, making it difficult to determine T$_{50}$ times. Generally, however, it appeared that a Na$^+$/K$^+$ gradient did not significantly increase the retention times for vesicles of this composition. The measured data showed that in 24 hours approximately 44% of the drug was released, irrespective of whether or not a transmembrane Na$^+$/K$^+$ gradient was used.

Part B

Use of pH Gradients to Reduce Drug Release Rates

Release of adriamycin from LUVs subsequent to active loading using the procedures of Example 1B was assayed as follows: vesicles (5 mM phospholipid) containing adriamycin were first passed over a 15 ml gel filtration column equilibrated in the appropriate buffer to remove free drug. The vesicle-containing fraction was then placed in a flow dialysis apparatus equilibrated at 37° C. Flow rates were adjusted to achieve total exchange of the sample compartment volume (50 ml) in 10 minutes. Aliquots (0.15 ml) were removed at various times and untrapped material was separated employing 1 ml gel filtration columns. The sample was then assayed for adriamycin and phospholipid.

Figure 8A:
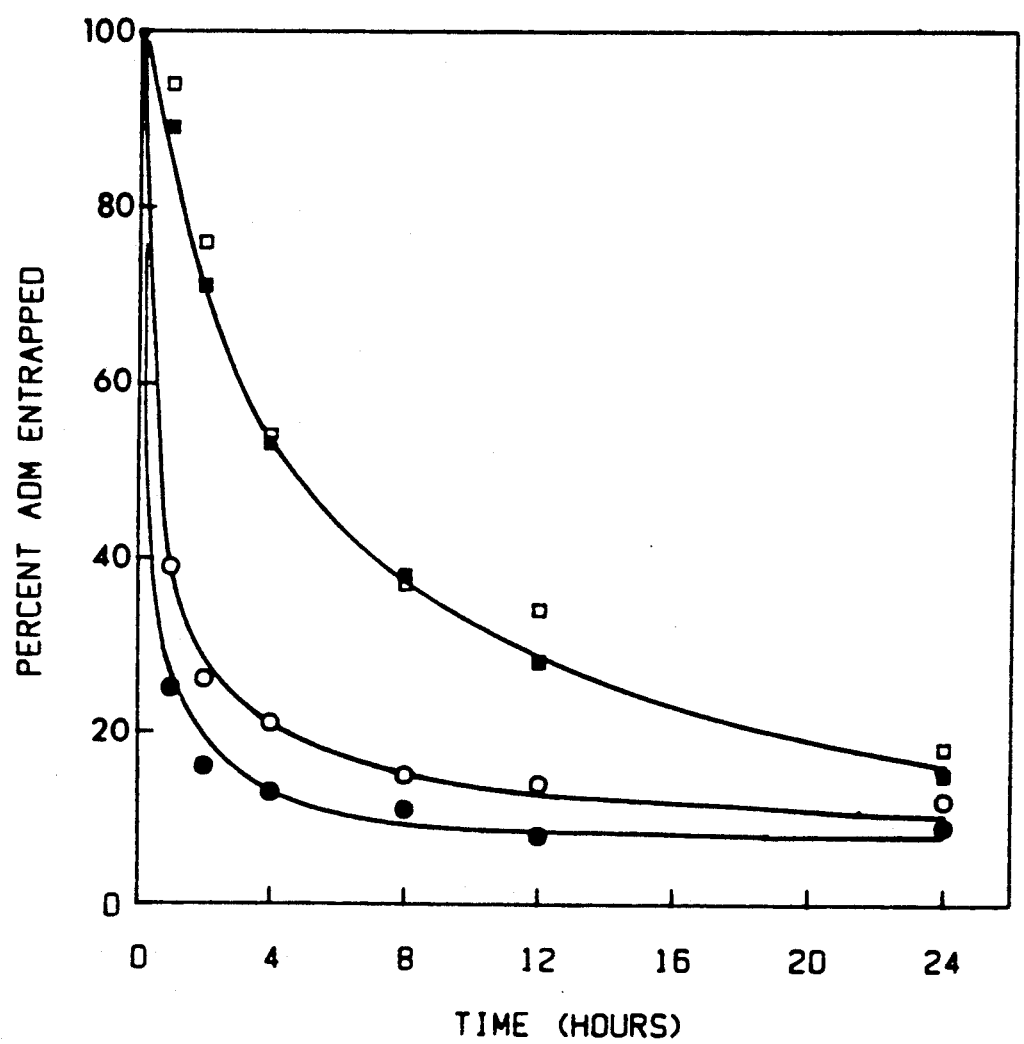
FIG. 8A-8B shows the release of adriamycin from EPC (solid circle, open circle) and EPC/cholesterol at a molar ratio of 1:1 (solid square, open square) LUVs at 37° C. Adriamycin was sequestered into vesicles in response to a pH gradient at lipid and drug concentrations of 5.0 and 0.5 mM, respectively. Free adriamycin was separated from vesicle-associated drug by gel filtration chromatography employing columns equilibrated in buffers adjusted to pH 4.6 (panel A) or pH 7.5 (panel B) which contained 150 mM $K^+$ (closed symbols) or 180 mM $Na^+$ (open symbols).
Figure 8B:
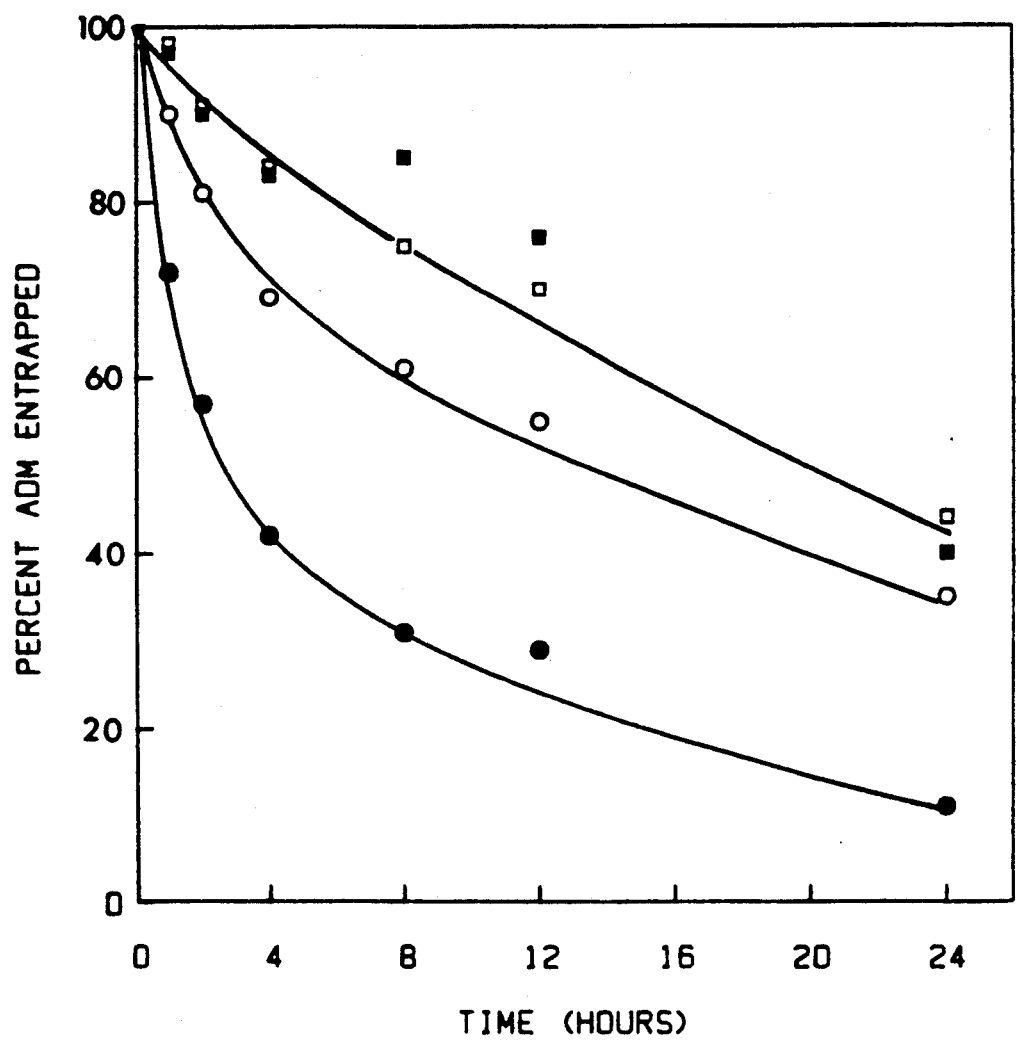

The release characteristics in the presence (panel B) and absence (panel A) of a pH gradient for EPC LUVs (circles) and EPC/cholesterol LUVs (squares) are shown in FIG. 8. The solid symbols represent release characteristics in the absence of a Na$^+$/K$^+$ gradient, while the open symbols represent the release characteristics in the presence of such a gradient. Specifically, in FIG. 8A adriamycin-containing vesicles were passed down desalting columns equilibrated in buffers adjusted to pH 4.6, identical to the interior pH, whereas in FIG. 8B, the exterior pH was maintained at 7.5 during separation of free from vesicle-associated drug.

As shown in FIG. 8, in all cases, elimination of the transmembrane pH gradient dramatically increased the rate of adriamycin efflux. Decreasing the exterior pH from 7.5 to 4.6, in the absence of Na$^+$/K$^+$ gradient (solid symbols) decreased the time for 50 percent release of trapped drug from approximately 24 to 4 hours for EPC/cholesterol LUVs (squares) and from 3 to less than 1 hour for EPC LUVs (circles). No significant effect on release kinetics was observed for EPC/cholesterol vesicles when both a pH gradient and a Na$^+$/K$^+$ were used instead of just a pH gradient (compare solid and open squares). For the egg PC systems, however, the combination of a pH gradient and a Na$^+$/K$^+$ gradient resulted in longer retention times than those achieved with just a pH gradient (compare solid (pH only) and open (pH plus Na$^+$/K$^+$) circles). This effect was most pronounced for EPC LUVs in the presence of the transmembrane pH gradient (panel B), where the time for 50 percent adriamycin release increased from 3 to 16 hours when a Na$^+$/K$^+$ gradient was superimposed on the pH gradient. Note that a 16 hour T$_{50}$ value was also obtained for EPC vesicles using just a Na$^+$/K$^+$ gradient (see Table II).

EXAMPLE 3

Dehydration of Liposomes Containing an Antineoplastic Agent

This example illustrates the dehydration and subsequent rehydration of liposomes containing the antineoplastic agent adriamycin.

Egg phosphatidylcholine ETVs were prepared as described above using a solute solution (169 mM KGlu, 20 mM HEPES (pH 7.4), 40 umol lipid/ml) containing 250 mM trehalose. Subsequently, the external potassium buffer was exchanged for a sodium buffer (150 mM NaCl, 20 mM HEPES (pH 7.4), 250 mM trehalose). Adriamycin (200 nmol/umol lipid) was added, along with valinomycin (0.5 ug/umol lipid) to induce the membrane potential. After a 2 hour incubation, unencapsulated adriamycin was removed by passing the vesicles through a column of Sephadex G-50 equilibrated with the trehalose-containing sodium buffer described above. The ETVs were dehydrated for 24 hours without prior freezing and then rehydrated as described above.

The amounts of entrapped adriamycin in the vesicles both before and after dehydration/rehydration, as well as the rate of drug leakage from the vesicles, were measured using the assay described above (see "Assays") after passage of 100 ul aliquots of the vesicle suspension over columns (1 ml) of Sephadex G-50 to remove any untrapped material (see U.S. Pat. Application Ser. No. 622,690 for further details). Since the columns tend to trap a small percentage of the liposomes applied thereto, the measured values for the amounts of encapsulated material retained after the dehydration/rehydration process are somewhat lower than the levels actually achieved by the procedures of the present invention.

The results of these experiments are shown in Table III. As shown therein, more than 90% of the drug is retained following dehydration and rehydration. Moreover, the rate of leakage of adriamycin from the rehydrated vesicles is comparable to the rate observed with vesicles which have not been dehydrated (data not shown).

EXAMPLE 4

Loading of Ionizable Antineoplastic Agents Into Rehydrated Liposomes Using Transmembrane Potentals This example illustrates: 1) that liposomes having a concentration gradient across their membranes can be dehydrated in the presence of a protective sugar and rehydrated without loss of the concentration gradient; and 2) that after rehydration, the concentration gradient can be used to load an ionizable antineoplastic agent (adriamycin) into the liposomes.

Vesicles having a Na$^+$/K$^+$ chemical gradient across their membranes were prepared by forming ETVs (40 umol lipid/ml) in a potassium glutamate buffer (169 mM potassium glutamate, 250 mM trehalose, 20 mM HEPES, pH 7.4), and then replacing the external buffer with a NaCl buffer (150 mM NaCl, 250 mM trehalose, 20 mM HEPES, pH 7.4) by passing the vesicles through a Sephadex G-50 column (1.4×10 cm) which had been pre-equilibrated with the NaCl solution. Where employed, valinomycin (Sigma, St. Louis, Missouri) was added in ethanol to a concentration of 0.5 ug/umole phospholipid.

Similarly, transmembrane pH gradients (interior acid) were formed by preparing the liposomes in a buffer with low pH (135 mM glutamic acid, 250 mM trehalose, brought to pH 5.5 by the addition of potassium hydroxide) which was then exchanged with a high pH buffer (125 mM glutamic acid, 30 mM NaCl, 250 mM trehalose, brought to pH 7.5 by the addition of potassium hydroxide) on a Sephadex G-50 column. Where used, the proton ionophore CCCP was added to a final concentration of 20 uM.

Transmembrane potentials were measured by determining the distribution of the lipophilic cation $^3$H-tetraphenylphosphonium bromide ($^3$H-TPPB, NEN, Canada). Specifically, 1 uCi of 3H-TPPB in 1 ul ethanol was added to a 1-2 ml sample of the ETV dispersion and the mixture was incubated at 20° C. for 20 minutes. An aliquot (100 ul) was withdrawn and the untrapped $^3$H-TPP$^+$ was removed by loading the aliquot onto a Sephadex G-50 column packed in a 1 ml disposable syringe, and then centrifuging the column at 500 g for 3 minutes to elute the vesicles. The trapped $^3$H-TPP$^+$ was determined by liquid scintillation counting, and the phospholipid determined by phosphate assay.

Using trapped volume values (ul per umol of phospholipid) for the ETVs determined by measuring the amount of $^{22}$Na, $^3$H-inulin or $^{14}$C-inulin captured in the ETVs by the ETV process, the concentrations of $^3$H-TPP$^+$ inside [$^3$H-TPP$^+$]$_i$ and outside [$^3$H-TPP$^+$]$_o$ the vesicles were calculated, from which the transmembrane potential ($V_m$) was calculated using the Nernst equation:

$$V_m = -59 \log [^3H\text{-}TPP^+]_i/[^3H\text{-}TPP^+]_o$$

Figure 9:
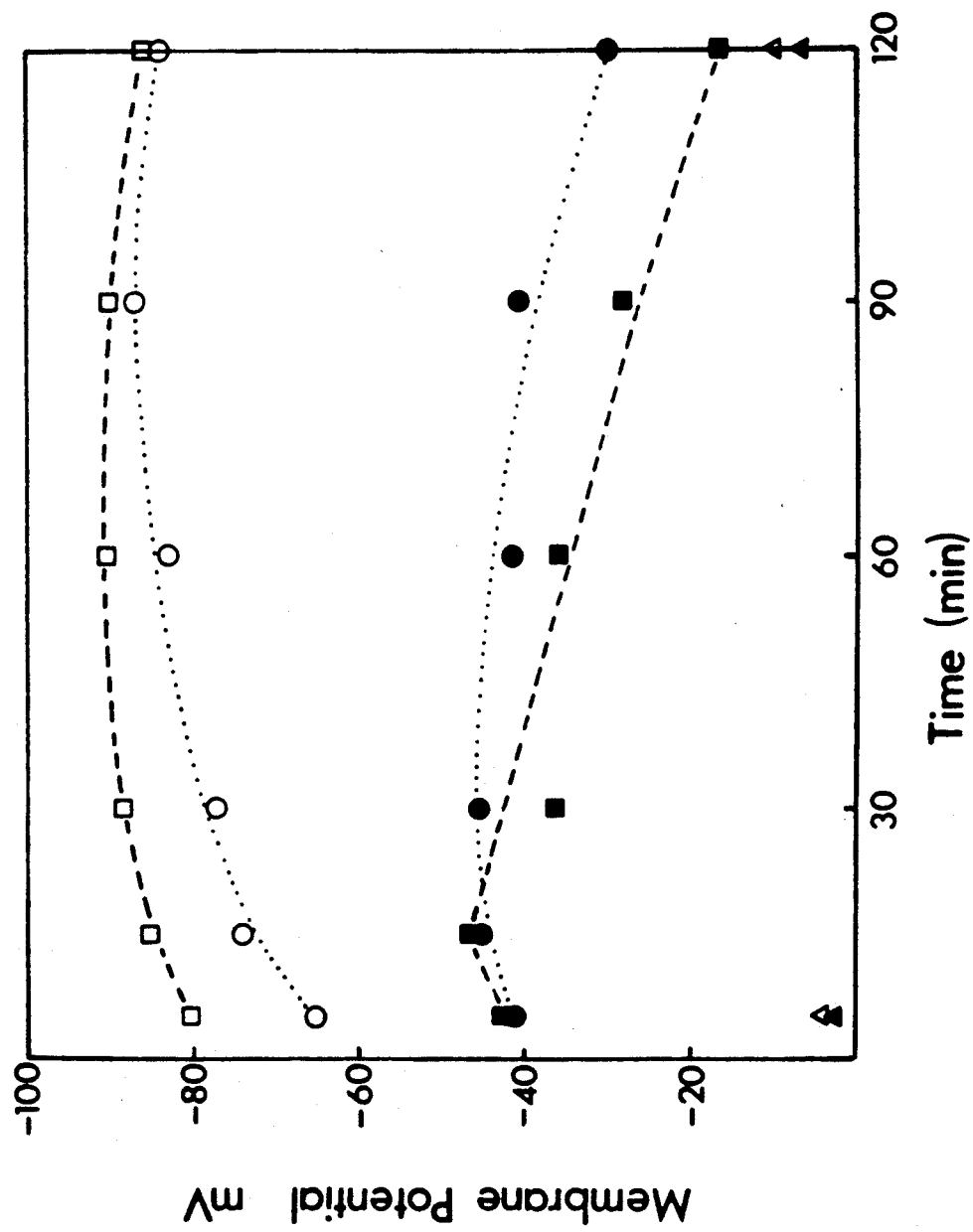
FIG. 9 shows the transmembrane potentials generated by a pH gradient for control vesicles (squares) and dehydrated/rehydrated vesicles (circles). Vesicles with a pre-existing proton gradient were maintained at 4° C. for 24 hours (control) or dehydrated in the presence of 250 mM trehalose under high vacuum for the same period of time. The potential observed in the vesicles upon rehydration was determined in the absence of CCCP (open circles and squares), or with 20 uM CCCP present (solid circles and squares), using the probe $^3$H-tetraphenylphosphonium bromide. The transmembrane potentials observed in vesicles without a pH gradient in the presence and absence of CCCP is shown by the solid and open triangles, respectively.
Figure 10:
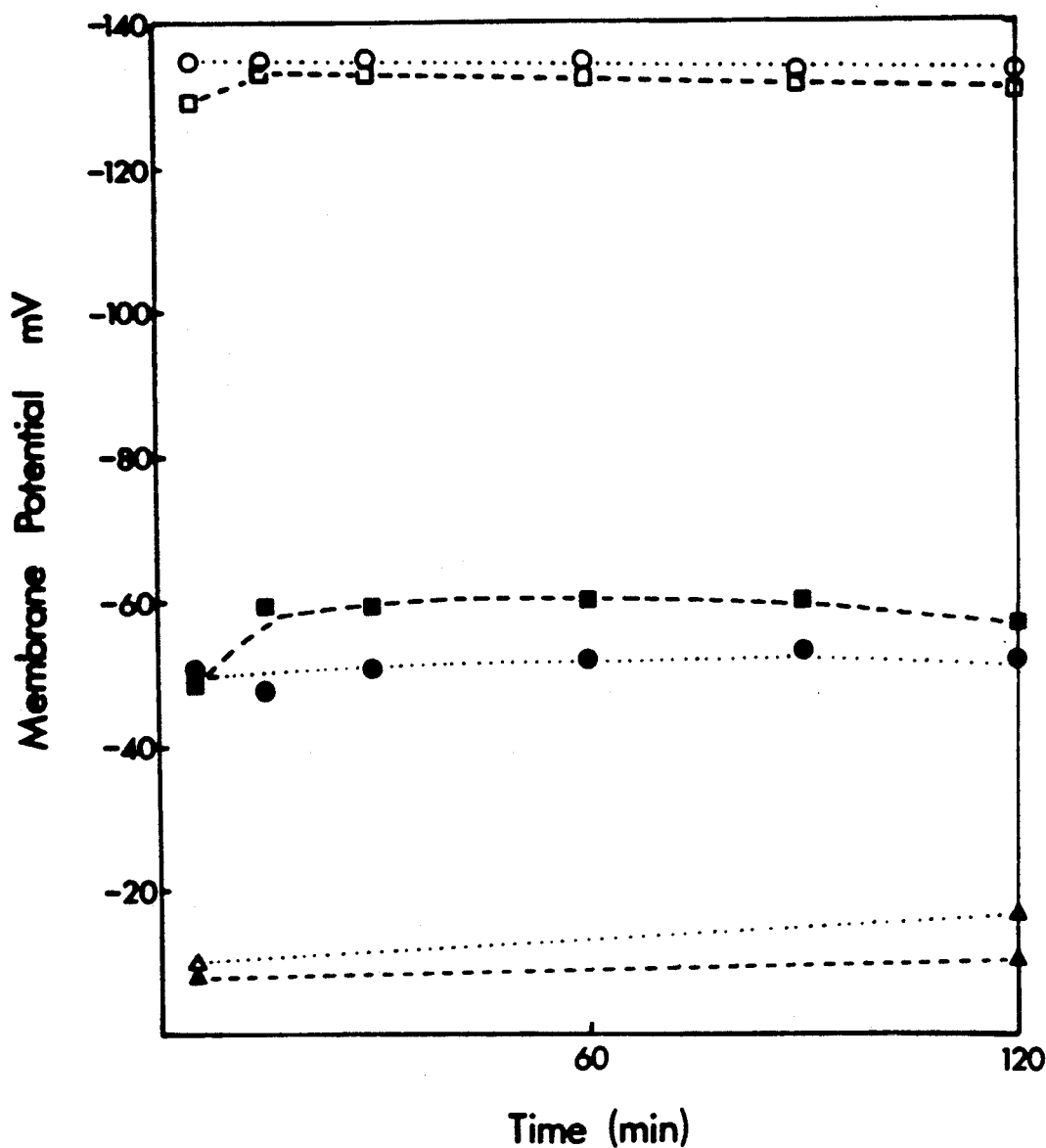
FIG. 10 shows the transmembrane potentials generated by a $Na^+/K^+$ chemical gradient for control vesicles (squares) and dehydrated/rehydrated vesicles (circles). Vesicles with a pre-existing $Na^+/K^+$ gradient were maintained at 4° C. for 24 hours (control) or dehydrated in the presence of 250 mM trehalose under high vacuum for the same period of time. The potential observed in the vesicles upon rehydration was determined in the absence of valinomycin (solid circles and squares), or with 0.5 ug/umole phospholipid valinomycin present (open circles and squares), using the probe $^3$H-tetraphenylphosphonium bromide. The transmembrane potentials observed in vesicles having potassium glutamate on both sides of the membrane in the presence and absence of valinomycin is shown by the open and solid triangles, respectively.

Both the Na$^+$/K$^+$ and the pH gradient vesicles were dehydrated under high vacuum for 24 hours and then rehydrated. Control vesicles were kept at 4° C. for 24 hours. Following drying and rehydration, the transmembrane potentials exhibited by these vesicles in the presence and absence of ionophores were compared to the transmembrane potentials generated by the controls, also in the presence and absence of ionophores. The results are shown in FIGS. 9 (pH) and 10 (Na$^+$/K$^+$).

As can be seen from these figures, the transmembrane potentials exhibited by the vesicles which had been dehydrated and then rehydrated are essentially identical to those exhibited by the controls. The only apparent difference is that in the case of the pH gradient vesicles, the transmembrane potentials for the dehydrated/rehydrated vesicles develop somewhat slower than the transmembrane potentials for the control vesicles.

The ability of the Na$^+$/K$^+$ vesicles to accumulate adriamycin after dehydration and rehydration was tested in the presence and absence of the ionophore valinomycin, and compared with the accumulation exhibited by the control vesicles, i.e., the vesicles which had been stored at 4° C. for 24 hours rather than being dehydrated for 24 hours. Sufficient adriamycin was added to the vesicles' external medium to produce a final concentration of 0.2 moles adriamycin per mole of phospholipid.

Figure 11:
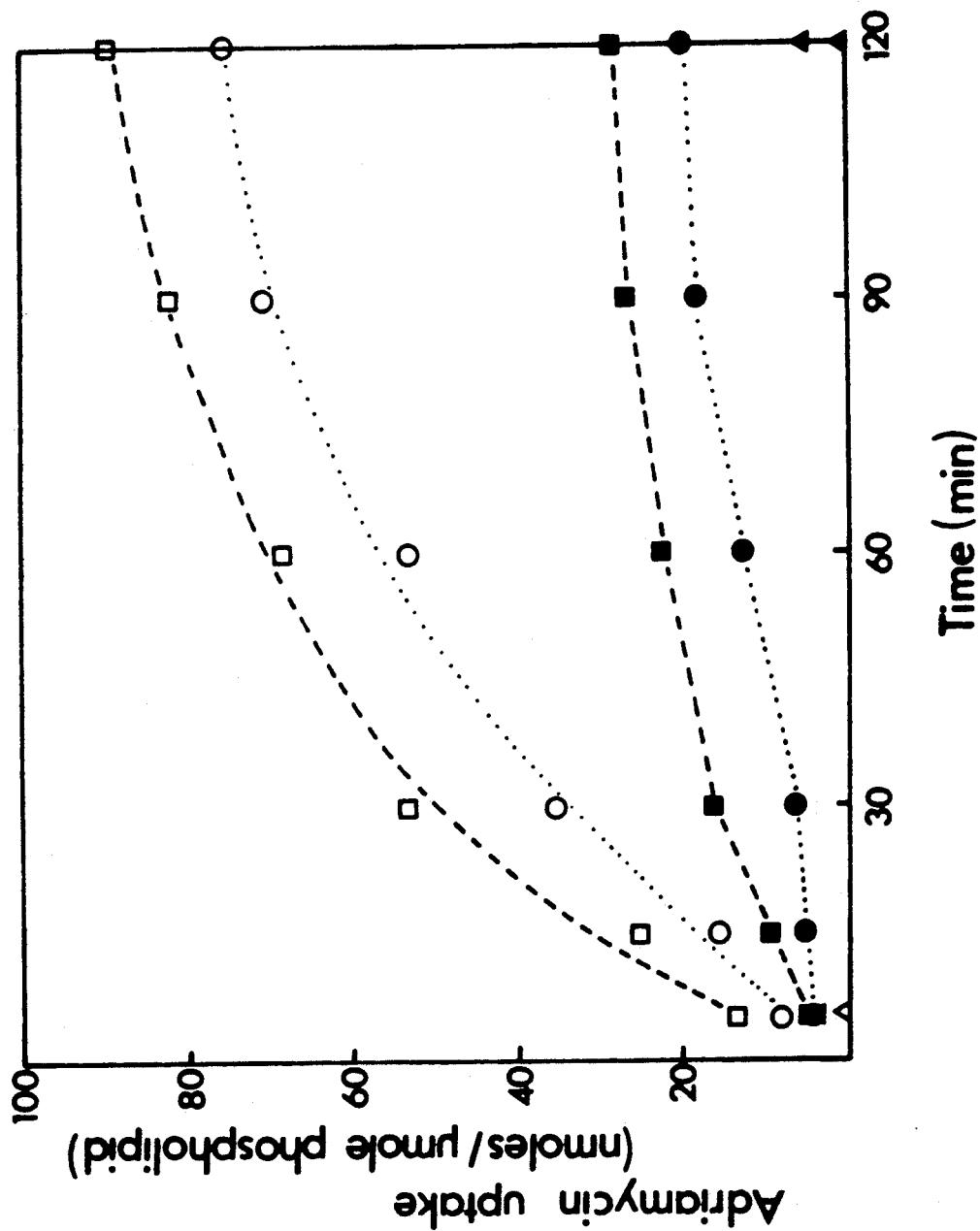
FIG. 11 illustrates the use of a transmembrane potential to load adriamycin into previously dried vesicles. Vesicles with a pre-existing $Na^+/K^+$ gradient were dehydrated for 24 hours in the presence of 250 mM trehalose. Following rehydration the ability of the vesicles to accumulate adriamycin in the presence (open circles), or absence (solid circles) of valinomycin (0.5 ug/umole phospholipid) was measured. Control vesicles maintained at 4° C. for the same period were also tested in the presence (open squares) or absence (solid squares) of valinomycin.

The results of these tests are shown in FIG. 11. As can be seen therein, the dehydrated/rehydrated vesicles accumulate adriamycin essentially at the same rate and to the same extent as the control vesicles. Accordingly, this example demonstrates that delayed loading of vesicles can be accomplished through the combination of concentration gradients and the dehydration/rehydration process.

TABLE I

| ACTIVE/PASSIVE TRAPPING OF ANTINEOPLASTIC AGENTS IN LIPOSOMES | | |
|---|---|---|
| Drug | Trapping Efficiency (%) | nmol drug per umol lipid |
| Methotrexate + | 33 | 35.3 |
| adriamycin | 99 | 99 |
| Cytosine arabinoside + | 33 | 44.5 |
| adriamycin | 98 | 98 |
| Vinblastine | 90 | 36 |
| Adriamycin | 95 | 95 |

Methotrexate was trapped passively at a concentration of 20 mM during preparation of vesicles (187 umol lipid/ml). Adriamycin was trapped employing a transmembrane Na$^+$/K$^+$ gradient in the presence of valinomycin with a vesicle concentration corresponding to 1 mM phospholipid and a starting adriamycin concentration of 100 uM. Cytosine arabinoside was trapped passively, at a concentration of 25 mM, during preparation of vesicles (187 umol lipid/ml), and vinblastine was trapped employing a transmembrane Na$^+$/K$^+$ gradient in the presence of valinomycin with a vesicle concentration corresponding to 5 mM phospholipid and a starting vinblastine concentration of 200 uM.

TABLE II

| DRUG RELEASE FROM LUVs IN THE PRESENCE AND ABSENCE OF A TRANSMEMBRANE POTENTIAL | | | |
|---|---|---|---|
| Lipid Composition | Agent Trapped | External Buffer | T$_{50}$(h) |
| Egg-PC | adriamycin | KCl | 1.5 |
| | | NaCl | 16 |
| Egg-PC/egg-PS(8:2) | adriamycin | KCl | 1.5 |
| | | NaCl | 6 |
| Egg-PC/Chol(1:1) | adriamycin | KCl | 4 |
| | | NaCl | 30 |

After drug encapsulation the external buffer and untrapped drug were replaced with either a KCl or NaCl buffer as specified. T$_{50}$ indicates the time needed for release of 50% of the trapped agent from the vesicles; Chol=cholesterol.

TABLE III

| ABILITY OF DEHYDRATED VESICLES TO RETAIN ADRIAMYCIN | |
|---|---|
| | Adriamycin Content (nmoles/umole lipid) |
| Before dehydration | 197 |
| Immediately after dehydration and rehydration | 185 |
| One hour after dehydration and rehydration | 158 |
| Two hours after dehydration and rehydration | 145 |

What is claimed is:

1. A method for reducing the rate of release of an ionizable, biologically-active agent from liposomes comprising generating a transmembrane potential across the liposome membranes which has an orientation such that if the agent is positively charged, the internal potential of the liposomes is negative relative to the potential of the external medium, and if the agent is negatively charged, the internal potential of the liposomes is positive relative to the potential of the external medium.

2. The method of claim 1 wherein the transmembrane potential is generated by creating a concentration gradient of one or more charged species across the liposome membranes.

3. The method of claim 2 wherein the concentration gradient is a $Na^+/K^+$ concentration gradient.

4. The method of claim 2 wherein the concentration gradient is a pH gradient.

5. The method of claim 1 wherein the agent is an antineoplastic agent.

6. The method of claim 5 wherein the antineoplastic agent is selected from the group consisting of daunorubicin, doxorubicin, vinblastine, and pharmaceutically acceptable salts and derivatives thereof.

7. A pharmaceutical preparation comprising liposomes having encapsulated therein an ionizable, biologically-active agent, said liposomes having a transmembrane potential across their membranes, the orientation of the transmembrane potential being such that if the agent is positively charged in its ionized form, the internal potential of the liposomes is negative relative to the potential of the external medium, and if the agent is negatively charged in its ionized form, the internal potential of the liposomes is positive relative to the potential of the external medium, and wherein for an agent which is positively charged in its ionized form, the concentration of the agent in the liposomes is at least about 20 mM, or wherein the concentration of the agent in the liposomes is at least about 20 mM and the ratio of the concentration of the agent inside the liposome to the concentration of the agent in the external medium is at least about 140.

8. The pharmaceutical preparation of claim 7 wherein the transmembrane potential has been produced by creating a concentration gradient of one or more charged species across the liposome membranes.

9. The pharmaceutical preparation of claim 8 wherein the concentration gradient is a $Na^+/K^+$ concentration gradient.

10. The pharmaceutical preparation of claim 8 wherein the concentration gradient is a pH gradient.

11. The pharmaceutical preparation of claim 7 wherein the agent is an antineoplastic agent.

12. The pharmaceutical preparation of claim 11 wherein the antineoplastic agent is selected from the group consisting of daunorubicin, doxorubicin, vinblastine, and pharmaceutically acceptable salts and derivatives thereof.

13. A pharmaceutical preparation comprising liposomes having two or more antineoplastic agents encapsulated therein, wherein at least one of the agents is ioniable, said liposomes having a transmembrane potential across their membranes, the orientation of the transmembrane potential being such that if the ionizable agent is positively charged in its ionized form, the internal potential of the liposomes is negative relative to the potential of the external medium, and if the agent is negatively charged in its ionized form, the internal potential of the liposomes is positive relative to the potential of the external medium, and wherein for an agent which is positively charged in its ionized form, the concentration of the ionizable agent in the liposomes is at least about 20 mM, or wherein the concentration of the ionizable agent in the liposomes is at least about 20 mM and the ratio of the concentration of the ionizable agent inside the liposome to the concentration of the ionizable agent in the external medium is at least about 140.

14. The pharmaceutical preparation of claim 13 wherein one of the antineoplastic agents is an ionizable antineoplastic agent.

15. The pharmaceutical preparation of claim 14 wherein the ionizable antineoplastic agent has been loaded into the liposomes by means of a transmembrane potential.

16. The pharmaceutical preparation of claim 15 wherein the ionizable antineoplastic agent is doxorubicin.

17. The pharmaceutical preparation of claim 15 wherein the two or more antineoplastic agents include doxorubicin and methotrexate.

18. The pharmaceutical preparation of claim 15 wherein the two or more antineoplastic agents include doxorubicin and cytosine arabinoside.

19. A method of treating neoplasms comprising administering an antineoplastic effective amount of the pharmaceutical preparation of claim 11.

20. A method of treating neoplasms comprising administering an antineoplastic effective amount of the pharmaceutical preparation of claim 13.

* * * * *